(12) United States Patent
Nayak

(10) Patent No.: US 7,549,974 B2
(45) Date of Patent: Jun. 23, 2009

(54) DEVICE AND METHOD FOR MEDICAL INTERVENTIONS OF BODY LUMENS

(75) Inventor: Asha Shrinivas Nayak, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 488 days.

(21) Appl. No.: 10/449,695

(22) Filed: May 30, 2003

(65) Prior Publication Data
US 2004/0049152 A1 Mar. 11, 2004

Related U.S. Application Data

(60) Provisional application No. 60/384,451, filed on Jun. 1, 2002.

(51) Int. Cl.
A61M 29/00 (2006.01)

(52) U.S. Cl. ................. 604/96.01; 604/103.06

(58) Field of Classification Search ............ 604/103.11, 604/509, 194, 916, 103, 96.01, 103.06, 101.02, 604/103.07, 103.09, 103.14, 103.12; 606/192, 606/194, 198
See application file for complete search history.

(56) References Cited

U.S. PATENT DOCUMENTS

| 3,939,820 | A | * | 2/1976 | Grayzel ................ 600/18 |
| 5,074,845 | A | * | 12/1991 | Miraki et al. ........ 604/103.08 |
| 5,387,225 | A | | 2/1995 | Euteneuer et al. ........ 606/194 |
| 6,013,085 | A | | 1/2000 | Howard ................ 606/108 |
| 6,048,350 | A | | 4/2000 | Vrba ................... 606/108 |
| 6,124,007 | A | * | 9/2000 | Wang et al. ............ 428/35.2 |
| 6,126,634 | A | * | 10/2000 | Bagaoisan et al. ..... 604/101.02 |
| 6,146,370 | A | | 11/2000 | Barbut ................ 604/500 |
| 6,206,868 | B1 | | 3/2001 | Parodi ................ 604/500 |
| 6,261,260 | B1 | * | 7/2001 | Maki et al. ........... 604/103.07 |
| 6,295,989 | B1 | | 10/2001 | Connors, III .......... 128/898 |
| 6,312,444 | B1 | | 11/2001 | Barbut ................ 606/200 |
| 6,319,229 | B1 | | 11/2001 | Kim et al. ............ 604/103 |
| 6,413,235 | B1 | | 7/2002 | Parodi ................ 604/104 |
| 6,423,032 | B2 | | 7/2002 | Parodi ................ 604/103.07 |
| 6,540,712 | B1 | | 4/2003 | Parodi et al. .......... 604/6.14 |
| 6,558,401 | B1 | | 5/2003 | Azizi ................. 606/159 |
| 6,620,148 | B1 | * | 9/2003 | Tsugita ............... 604/509 |
| 6,776,771 | B2 | * | 8/2004 | van Moorlegem et al. ............ 604/101.01 |
| 2001/0044598 | A1 | | 11/2001 | Parodi |
| 2002/0016564 | A1 | | 2/2002 | Courtney et al. |
| 2002/0049408 | A1 | | 4/2002 | Van Moorlegem et al. |

(Continued)

Primary Examiner—Nicholas D Lucchesi
Assistant Examiner—Christopher D Koharski
(74) Attorney, Agent, or Firm—Lumen Patent Firm

(57) ABSTRACT

A directional balloon is provided that can be used for a medical intervention of a body lumen. In one aspect, the directional balloon inflates in a distal to proximal direction and deflates in a proximal to distal direction. In another aspect, the directional balloon inflates in a proximal to distal direction and deflates in a distal to proximal direction. The directional balloon is capable of providing an occlusive seal to protect against embolization. A suction catheter with a control means is provided to provide suction in a controlled fashion in a body lumen. The suction catheter is used during periods of a medical intervention that risks distal embolization. When turned on, the suction catheter is capable of removing unwanted materials. The suction means could be operated by a control means.

18 Claims, 41 Drawing Sheets

U.S. PATENT DOCUMENTS

| | | |
|---|---|---|
| 2002/0052620 A1 | 5/2002 | Barbut |
| 2002/0087119 A1 | 7/2002 | Parodi |
| 2002/0169436 A1 | 11/2002 | Gurm et al. |
| 2002/0169458 A1 | 11/2002 | Connors, III |
| 2002/0173815 A1 | 11/2002 | Hogendijk et al. |
| 2003/0074016 A1 | 4/2003 | Campbell et al. |

* cited by examiner

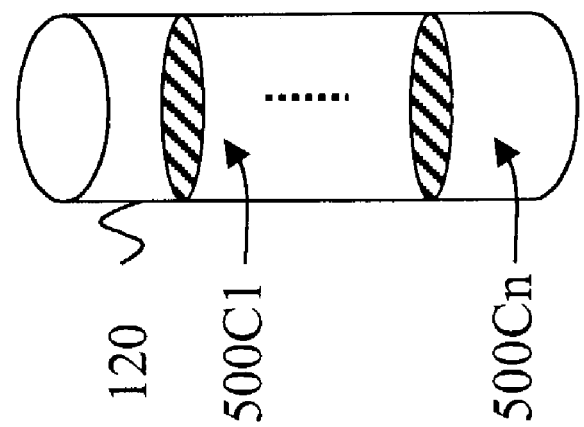
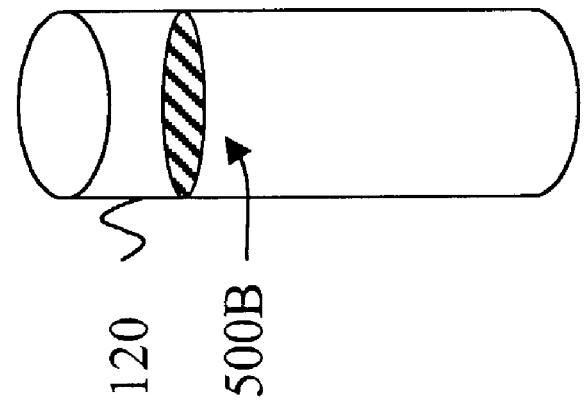
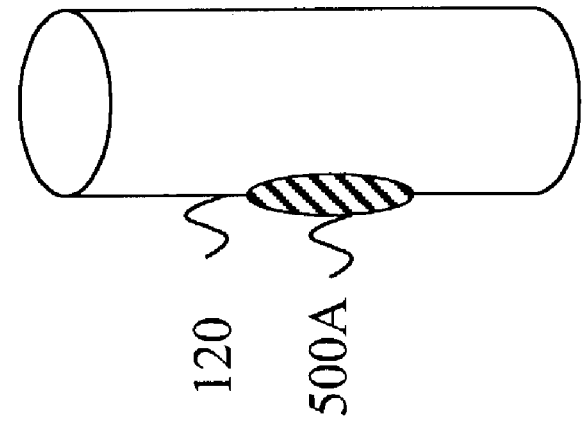
Figure 41

DEVICE AND METHOD FOR MEDICAL INTERVENTIONS OF BODY LUMENS

CROSS-REFERENCE TO RELATED APPLICATIONS

This application is cross-referenced to and claims priority from U.S. Provisional Application 60/384,451 filed Jun. 1, 2002, which is hereby incorporated by reference.

FIELD OF THE INVENTION

This invention relates generally to medical interventions. More particularly, the present invention relates to medical interventions in which body compartments with lumens, such as for example blood vessels, are being manipulated.

BACKGROUND

Physicians are increasingly performing catheter-based interventional procedures to treat common vascular diseases in which vessels are narrowed or occluded. Untreated, these conditions can lead to strokes, heart attacks, hypertension, or limb-threatening ischemia depending on the vessel involved. Despite physicians' intention to re-establish blood flow to vital organs, their interventional methods are frequently complicated by the liberation of unwanted material (e.g. clot, fat, and other debris). This results in embolization (blockage of distant blood vessels) and subsequent permanent end-organ damage, often with costly clinical consequences. Adequate distal embolic protection would ensure the safety of these important procedures, and is something physicians are in desperate need of. The prior art teaches several different solutions to the problem of distal protection that could generally be categorized as balloon occlusion devices, filtration devices and flow reversal devices. The following provides a brief description of these devices and their shortcomings.

Balloon Occlusion Devices

PercuSurge, Inc. was the first to recognize this clinical need and addressed it with a low-profile distal balloon system called the GuardWire. It is currently the only distal protection device approved by the FDA and, although only FDA-approved for cardiac applications, it is being routinely used off-label in carotid and other interventions. It requires the passage of a special hollow GuardWire past the narrowing and inflation of an occlusive balloon distal to the lesion. The balloon obstructs normal blood flow through the vessel, creating a barrier for debris, which can be suctioned away through a proximal suction catheter. Although physicians are pleased with its reduction in embolization rates, they still tend to be nervous about using the GuardWire because distal blood flow is completely stopped for the duration of the procedure. Especially in the brain and heart, this occlusion can be very poorly tolerated. With time, the distal tissues die, and thus physicians feel tremendously pressured for time while using this device. Further, it has recently been shown that the initial passage of the GuardWire across the unprotected lesion results in liberation of significant amounts of debris (See e.g. Orlandi et al. in a paper entitled "*Characteristics of cerebral microembolism during carotid stenting and angioplasty alone*", and published in *Archives of Neurology, Vol.* 58(9), September 2001, 1410-1413).

Filtration Devices

In an attempt to better preserve distal flow during protection, a generation of filter devices emerged which are currently in clinical trials. AngioGuard and FilterWire are large-profile umbrella-like devices, which are inserted (again past an unprotected lesion) into place, allowing blood to flow through the filters but trapping small debris, which cannot pass through its pores. Originally the devices were very bulky with 100 µm pores. Later versions have decreased the device profile and pore size down to 80 µm, decreasing the size of particles that are able to embolize through the filter. These filters, however, have several shortcomings in that (1) it is often difficult to get a large filter past a narrow occlusion, (2) there is no distal protection while the guidewire and filter are being inserted across the lesion, (3) they can fill with debris and lead to complete occlusion, (4) their metal edges can traumatize the vessel and cause vascular spasm, dissection, or perforation (5) small debris (<80 µm, which can cause significant end organ damage) can still pass through these filters (See e.g. Rapp et al. in a paper entitled "*Atheroemboli to the brain: size threshold for causing acute neuronal cell death*" and published in *Journal of Vascular Surgery, Vol.* 32(1): 68-76, July 2000), and (6) snug apposition of the filter against the vessel wall is difficult to ensure and thus a channel often persists for unprotected flow of debris to the distal vessels. It is of interest to note that animal studies have shown that debris as small as 15-40 µm can cause clinically significant embolization. Although the filter companies are aggressively trying to address these concerns, many of them are inherent to the filter concept, and an optimal solution with these devices is thought to be unlikely.

Flow Reversal Devices

Most recently, ArteriA, Inc. proposed a flow-reversal method, which employs an elaborate system of balloons and catheters to reverse the flow of blood across the lesion so that any debris that is liberated during the procedure flows directly into an external catheter where it can be filtered before being returned to the body via the venous system. While initially embraced in concept for use in the carotid/cerebral circulation, this idea has since met with many technical hurdles. First, only a fraction of patients are candidates for safe flow reversal, which requires an intact Circle of Willis (a highly anastomotic connection of arteries supplying the brain, which is notoriously variable in humans, and is only determined at the time of the procedure by cerebral arteriogram). Second, an elaborate system of catheters must be set up, including an extra-corporeal bypass tract which routes reversed blood back into the body after debris has been filtered out. This cumbersome setup is believed to limit the acceptance of this technology. Further, for the many stenotic lesions that occur in the common carotid artery, this technique would require withdrawal of a balloon past a fully deployed stent. Thus, this limits application of this technique only to stenoses entirely within the internal carotid artery, and not those that extend thru the carotid bifurcation into the common carotid artery.

Accordingly, there is a need to develop new and more effective solutions that can be used for catheter-based interventional procedures and desirably protect against embolization.

SUMMARY OF THE INVENTION

The present invention provides a device and method that can be used for a medical intervention of a body lumen. The device is a directional balloon that can be positioned in a body lumen. In one aspect of the present invention, the directional balloon inflates in a distal to proximal direction and deflates in a proximal to distal direction. In another aspect of the present invention, the directional balloon inflates in a proximal to distal direction and deflates in a distal to proximal direction.

The inflation and deflation of the directional balloon provides a milking action which could be performed once or repeatedly to achieve a desired effect.

The directional balloon could be used to prevent distal embolization, to manipulate unwanted materials within a body lumen, to appose a material to the wall of a body lumen, to manipulate an inserted device within a body lumen and/or to smooth out irregularities of a body lumen. The directional balloon is capable of providing an occlusive seal with a body lumen when the directional balloon is inflated. The directional balloon could be positioned in the body lumen so that the occlusive seal is distal to a region in the body lumen that requires a medical intervention.

To establish the directional action, the directional balloon could have a variable elasticity along its linear axis, different layers of materials, different shapes, at least one non-uniform material, different diameters along its linear axis, or the like. The dimensions of the directional balloon are dependent on the type of application. The type of material that could be used to manufacture the directional balloon should at least be flexible and biocompatible so that it can be used in a body lumen. However, the material of the directional balloon should be strong enough to provide an occlusive seal of at least one end of the directional balloon with a body lumen when the directional balloon is either partially or fully inflated. The flexibility of the directional balloon is desired for providing the milking action of the directional balloon. Also, in a preferred embodiment, the directional balloon of the present invention should be able to accommodate a guidewire to advance, position and retract the directional balloon in a body lumen.

In one aspect, a suction catheter is provided for use during a medical intervention in a body lumen. The suction catheter includes a control means to provide suction in a controlled fashion in a body lumen. Exemplary step-by-step scenarios of applications are included to show the control of the suction catheter. In a preferred embodiment, the suction catheter is used during periods of a medical intervention that risks distal embolization. When turned on, the suction catheter is capable of removing unwanted materials. To optimize suction, the suction catheter could include an occlusion means to either partially or fully occlude the suction catheter within a body lumen. The suction catheter could further include a filter means to filter unwanted materials. The suction means could be operated by a control means. Examples of a control means are for instance a voice recognition system, a hand or feet operated device, or a touch-screen device. The control means could also be automated.

BRIEF DESCRIPTION OF THE FIGURES

The objectives and advantages of the present invention will be understood by reading the following detailed description in conjunction with the drawings, in which like reference numerals refer to similar elements and in which:

Figure 1:
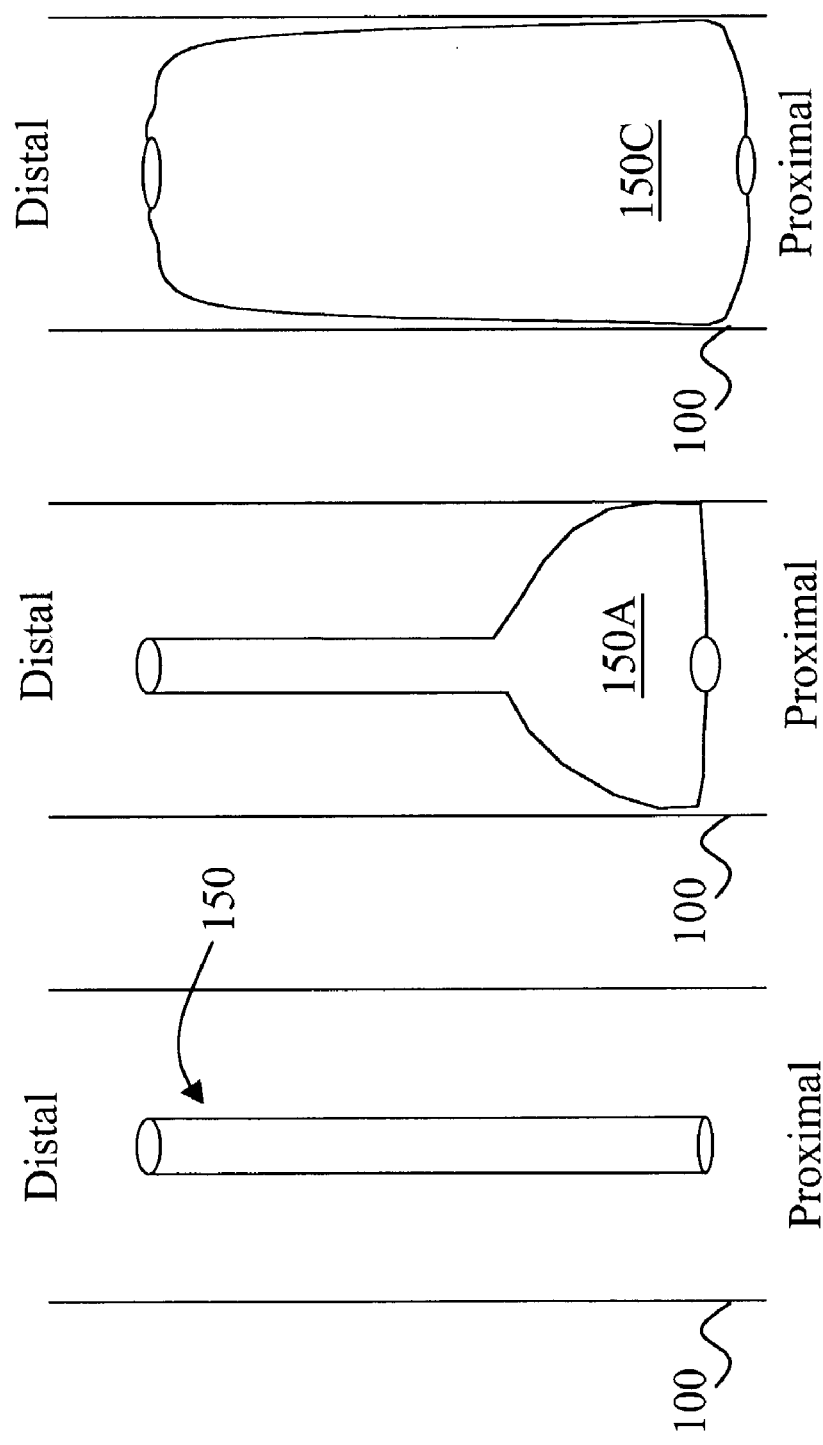
Figure 2:
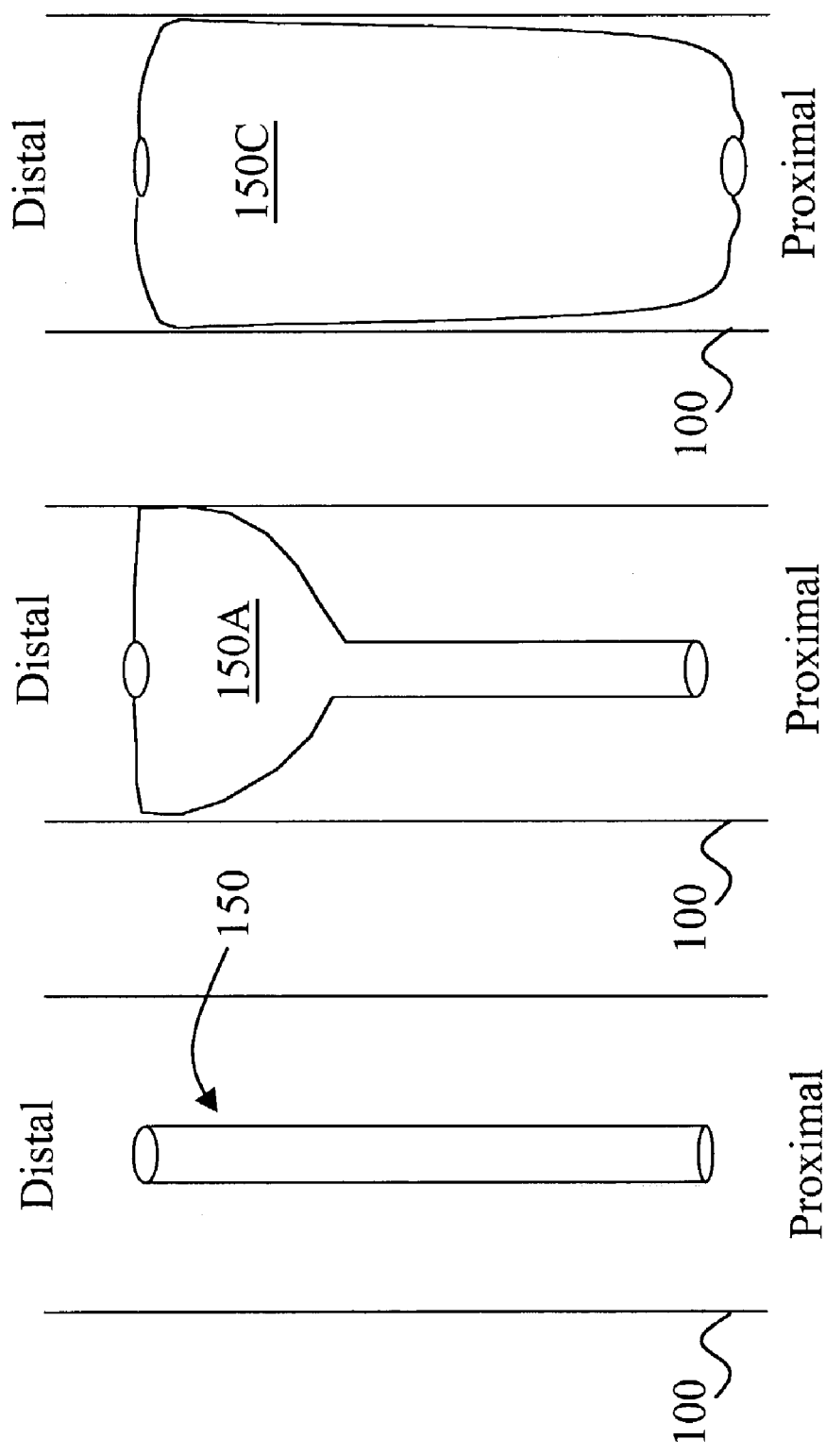
Figure 3:
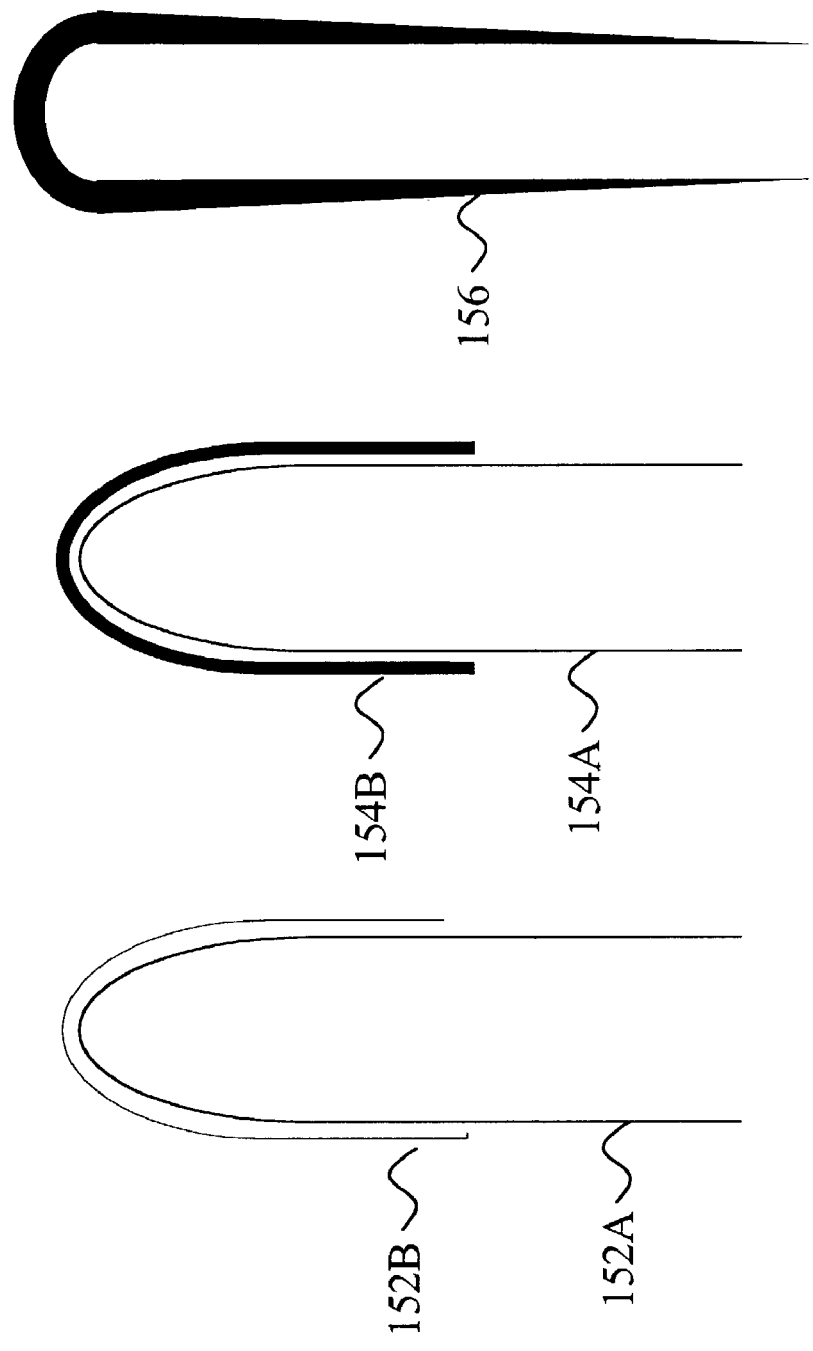

| | |
|---|---|
| FIGS. 1-3 | shows exemplary embodiment of a directional balloon according to the present invention; |
| FIGS. 4-19 | show an exemplary step-by-step scenario of an application of the directional balloon in a medical intervention that involves a carotid artery according to the present invention; |
| FIGS. 20-32 | show an exemplary step-by-step scenario of an application of the directional balloon in a medical intervention that involves stenting and postdilation of a carotid artery according to the present invention; |

Figure 32:
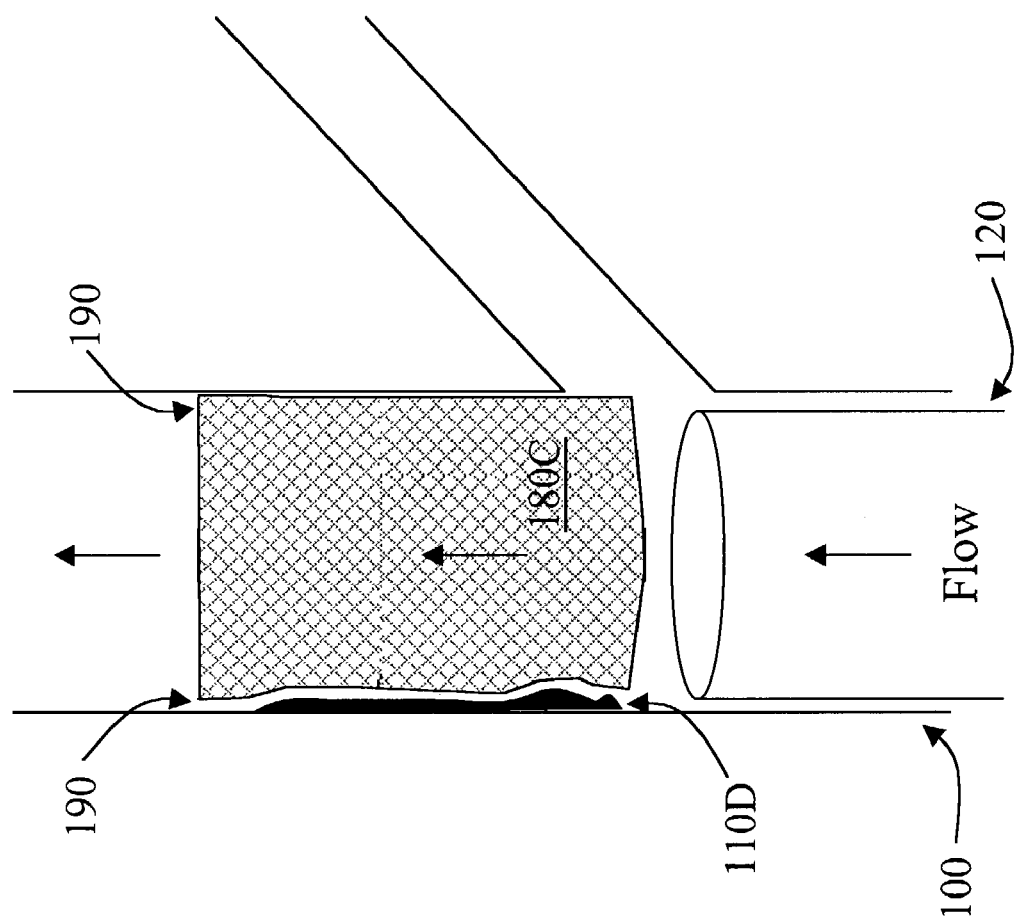
Figure 33:
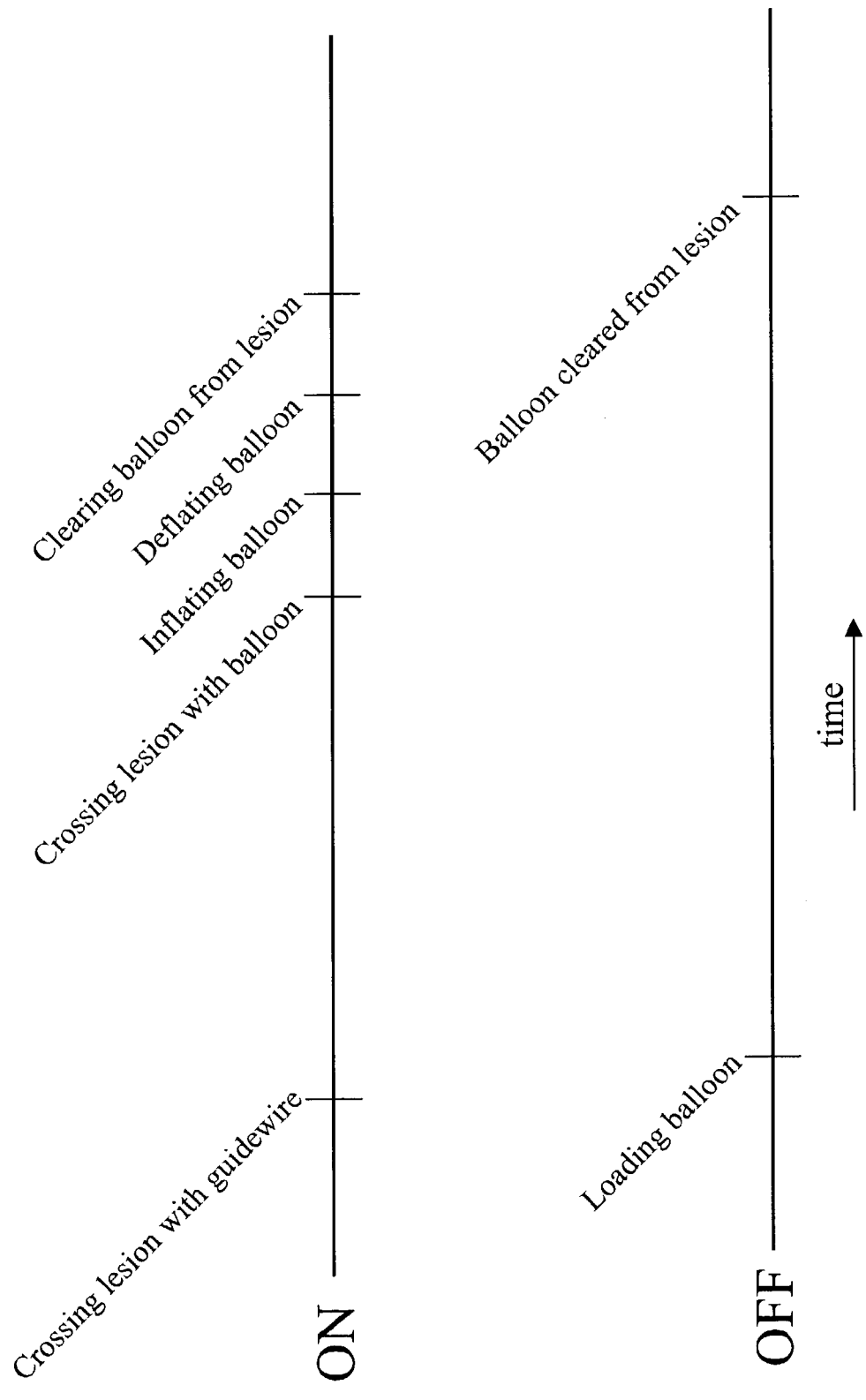
Figure 34:
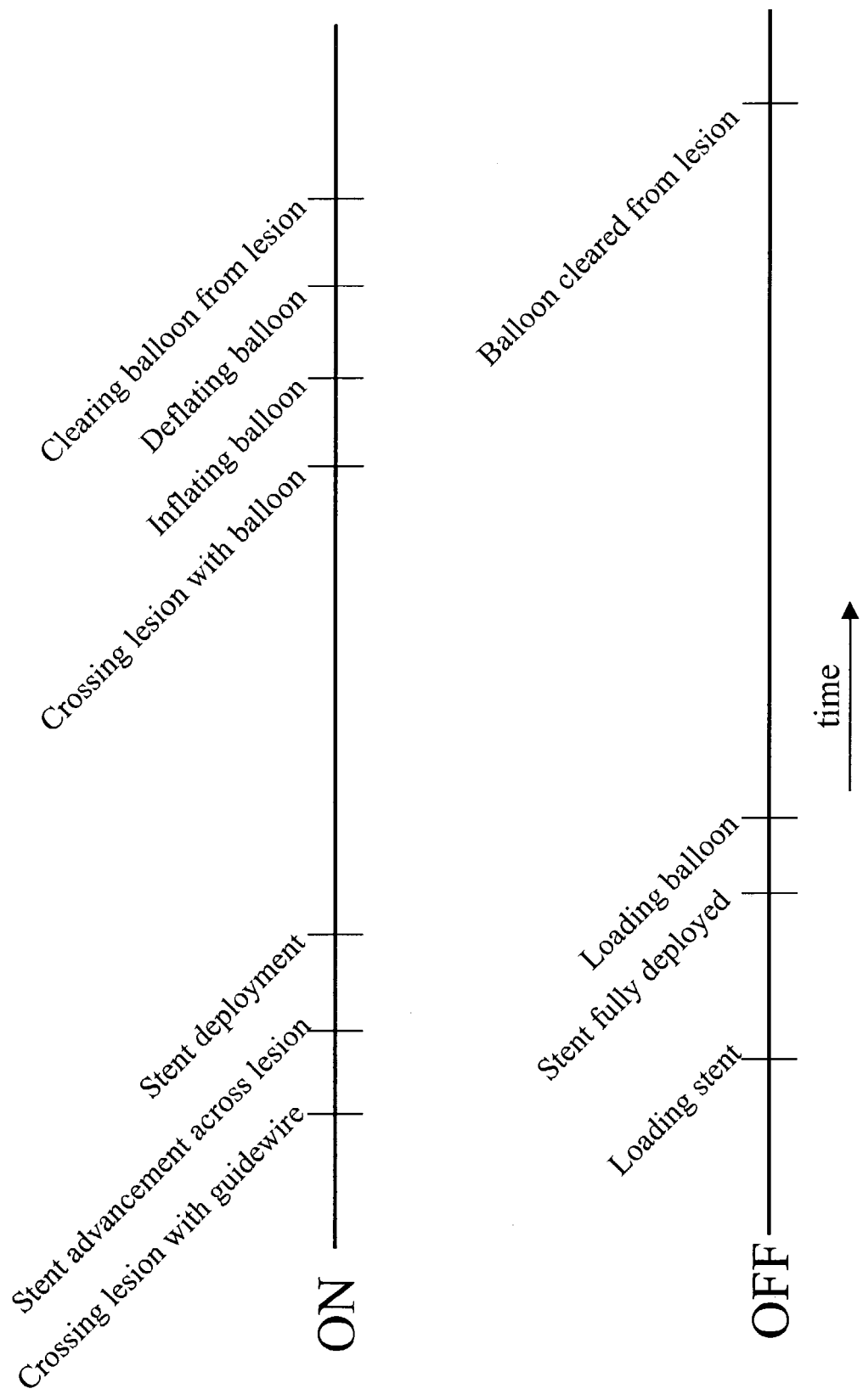
Figure 35:
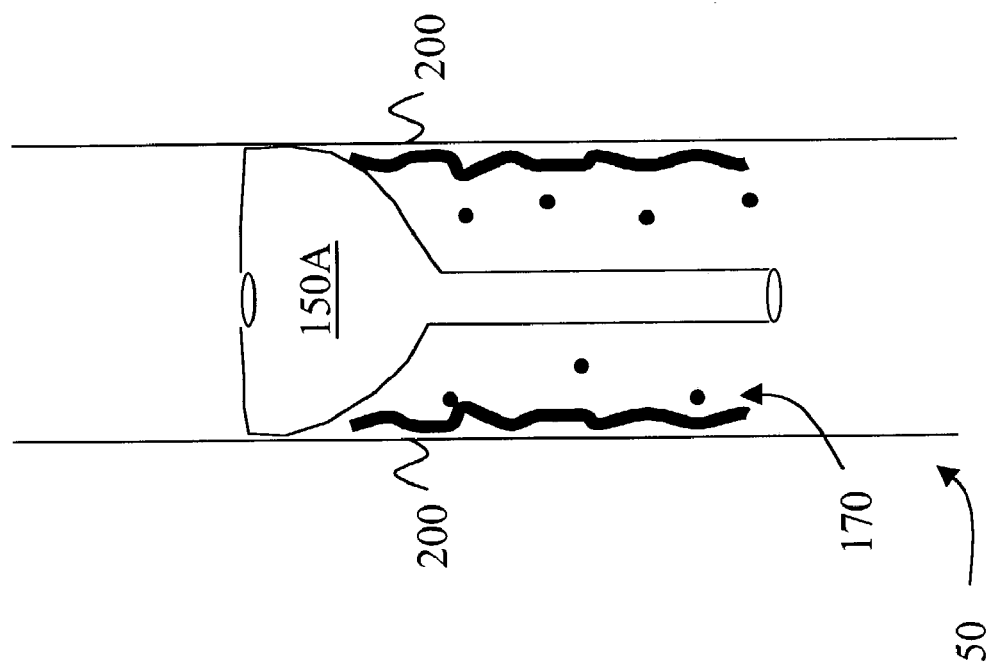
Figure 36:
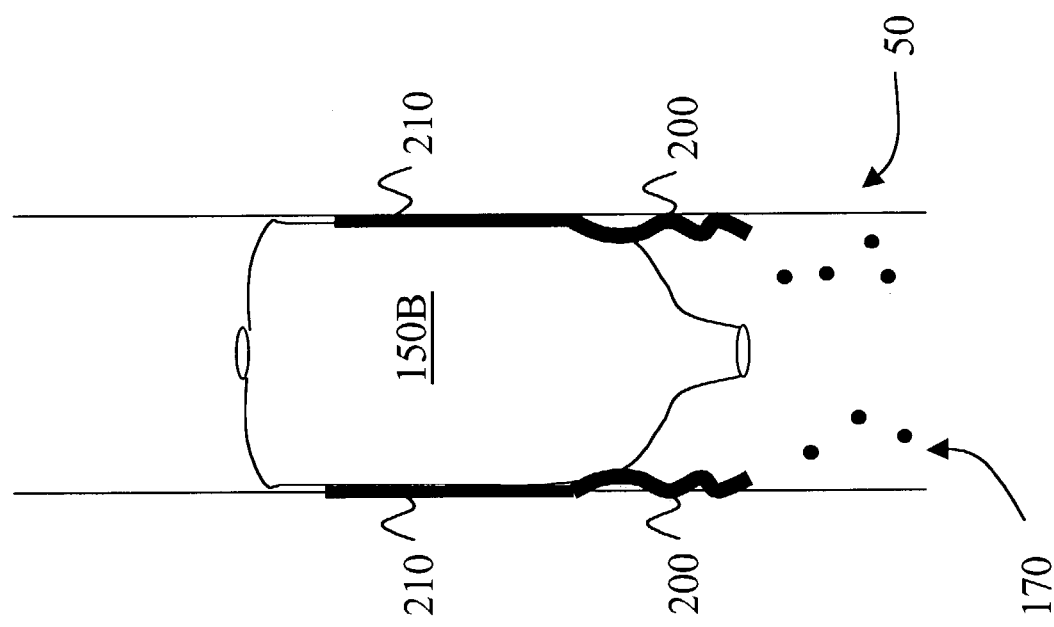
Figure 37:
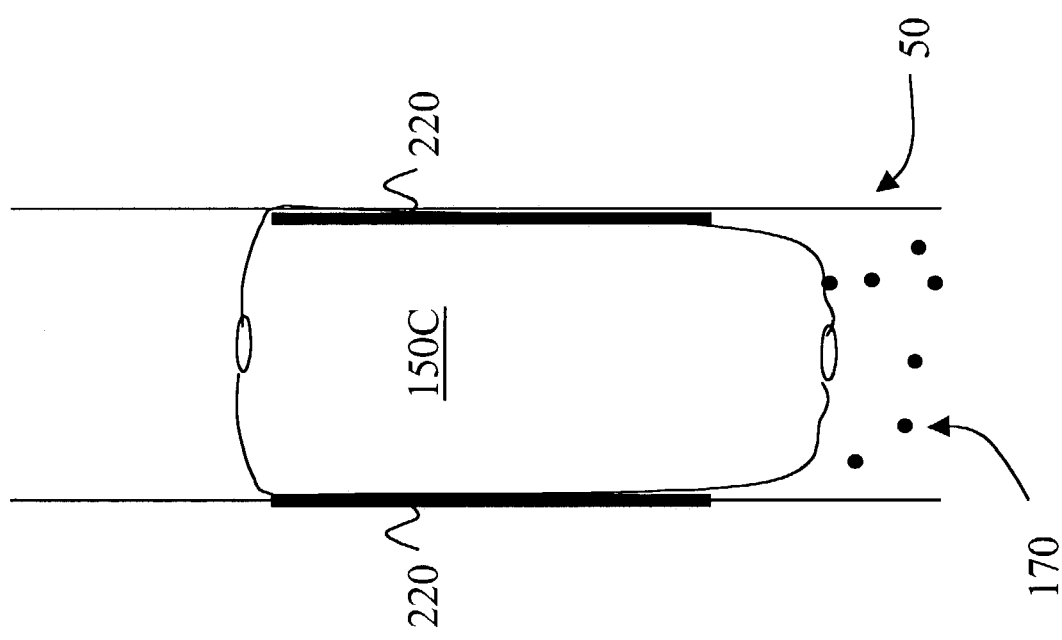
Figure 38:
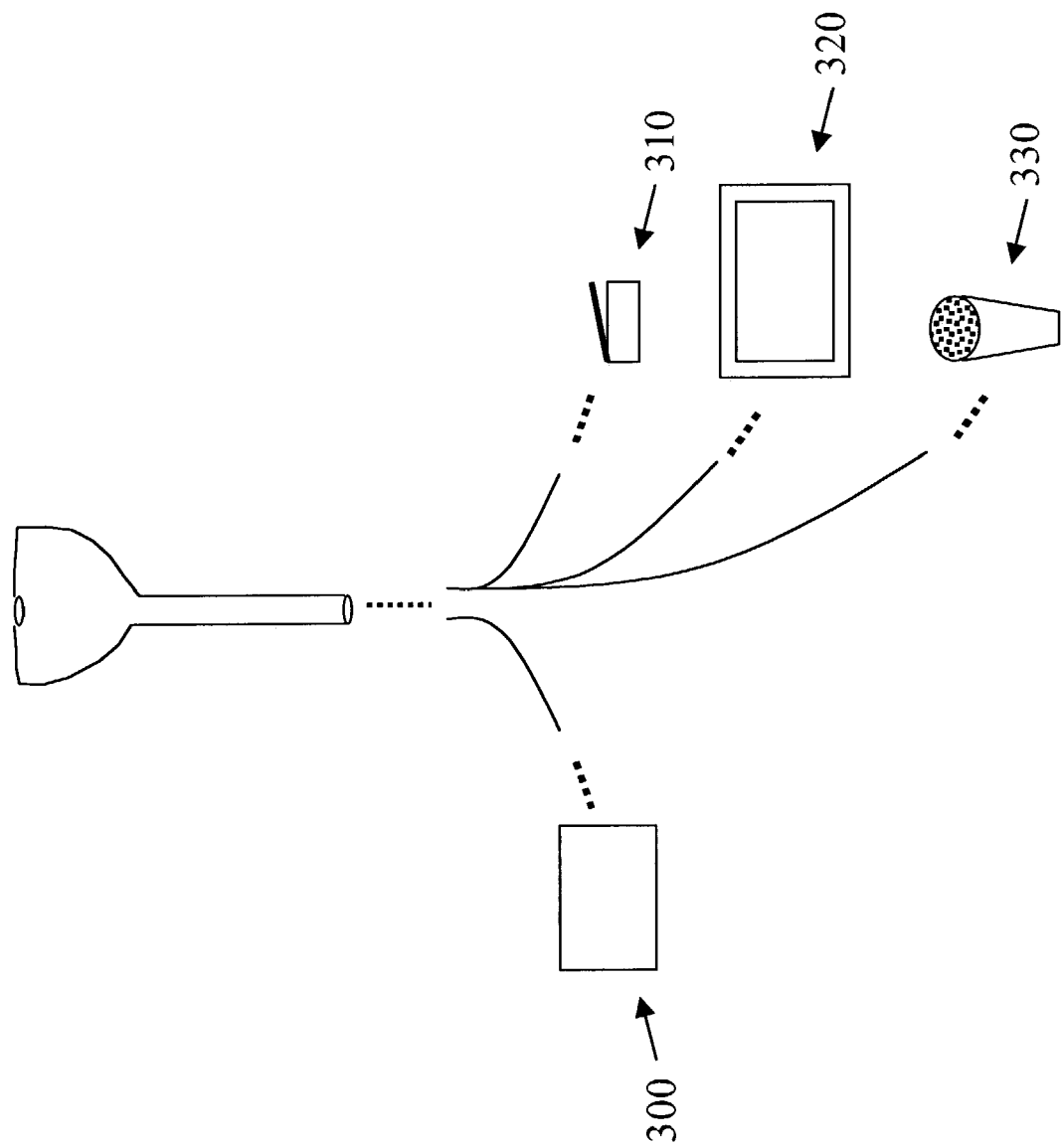
Figure 39:
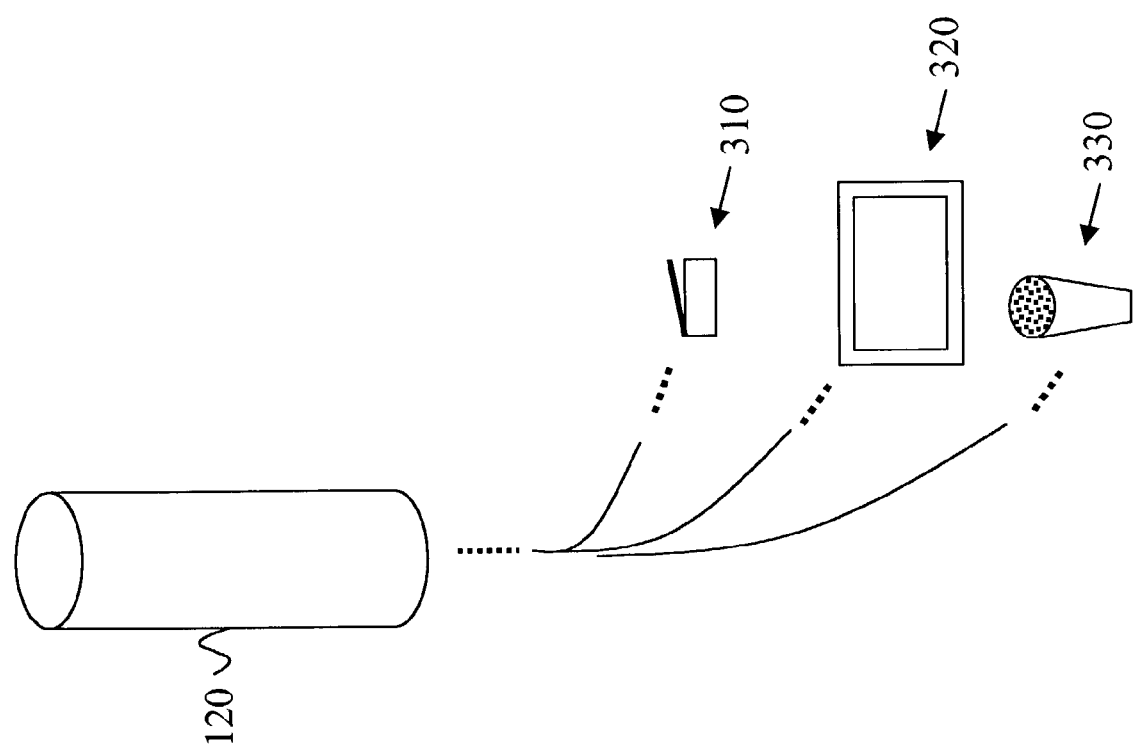
Figure 40:
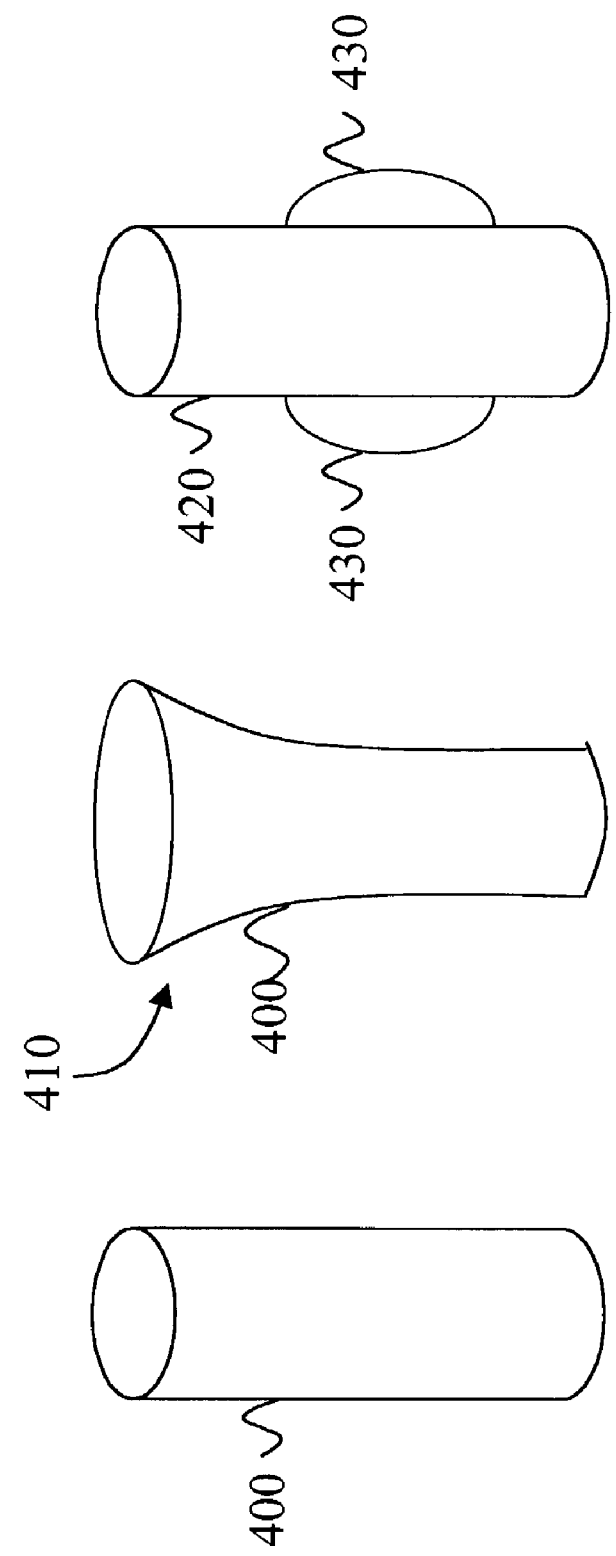

| | -continued |
|---|---|
| FIGS. 33-34 | summarize the time course of events during which the suction catheter is controlled in terms of being on or off for each of the two exemplary step-by-step scenarios related to FIGS. 4-19 and FIGS. 20-32 respectively; |
| FIGS. 35-37 | show an exemplary step-by-step scenario of an application of the directional balloon in a medical intervention that involves apposing a material to the wall of a body lumen according to the present invention; |
| FIG. 38 | shows an inflation/deflation means for the directional balloon as well as examples of control means to control the inflation/deflation of the directional balloon according to the present invention; |
| FIG. 39 | shows a suction catheter with examples of control means to control the suction according to the present invention; |
| FIG. 40 | shows exemplary embodiment of a suction catheter with means to partially or fully occlude the suction catheter with the body lumen according to the present invention; and |
| FIG. 41 | shows exemplary embodiments of a suction catheter with filter(s). |

LIST OF REFERENCE NUMBERS

| | |
|---|---|
| 50 | body lumen |
| 100 | carotid artery |
| 110 | region that requires medical intervention such as a lesion |
| 110B-D | reduction of region that requires medical intervention such as a lesion |
| 120 | suction catheter |
| 130 | guide wire |
| 140 | suction |
| 150 | directional balloon |
| 150A-E | partially (A-B, D-E) or fully (C) inflated directional balloon |
| 152A, B | balloons with different length but same elasticity |
| 154A, B | balloons with different length but different elasticity |
| 156 | balloon with graded elasticity along its linear axis |
| 160 | seal of distal portion of directional balloon with artery wall |
| 170 | unwanted materials |
| 170A-G | unwanted materials |
| 180 | stent |
| 180A-B | stent being deployed |
| 180C | fully deployed stent |
| 190 | seal of stent with artery wall |
| 200 | suction catheter with control means |
| 300 | inflation/deflation means |
| 310 | foot pedal |
| 320 | touchscreen |
| 330 | voice recognition |
| 400 | suction catheter with expandable tip 410 |
| 420 | suction catheter with balloons 430 to provide partial or total occlusion with a body lumen 50 |
| 500A, B, C1 . . . Cn | filter |

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention is aimed at medical interventional procedures inside a body lumen. In some cases it is desired or needed to protect against embolization during such medical intervention, which is therefore an additional aim of the present invention. The present invention described herein may be used in a variety of vascular and non-vascular settings, or in general, in a variety of body lumens. Applications of the present invention include interventions in coronary, carotid, neurovascular, renal, and peripheral circulations, as well as grafted anatomies, bypasses anatomies, fistulae, arteries, veins, and other natural or created body lumens, including passageways created through the interstitial space. The present invention may also be used in the urinary, gastrointestinal, biliary, cerebrospinal fluid, or lymphatic systems where fluids are known to flow through lumens. The balloon would also allow for safer penetration into narrow, occluded, or difficult to access compartments, for example, deep venous thromboses, pulmonary emboli, acute vascular occlusions, chronic total occlusions, or the like. The present invention may further be used for apposition procedures of materials to the wall of a body lumen. During this apposition procedure of a material, effective protection could also be provided against embolization. The present invention could further be used to smooth out irregularities of a body lumen while protecting against embolization.

The key idea of the present invention is to use a directional balloon during a medical intervention of a body lumen. In one aspect as shown in FIG. 1, with respect to the anatomical nomenclature of distal and proximal, the directional balloon is positioned in the body lumen and is capable of being inflated in a proximal to distal direction and being deflated in a distal to proximal direction. In another aspect as shown in FIG. 2, with respect to the anatomical nomenclature of distal and proximal, the directional balloon is positioned in the body lumen and is capable of being inflated in a distal to proximal direction and being deflated in a proximal to distal direction.

How the directional balloon should be used depends on the type of medical intervention at hand. For instance, if it is important to protect against distal embolization, then it would be desired that the directional balloon be inflated in a distal to proximal direction and deflated in a proximal to distal direction. In another example, if the medical intervention is geared towards apposing a material to or smoothing out irregularities in a body lumen, then the directional balloon may be inflated from either single side towards the other side such that the directional balloon provides a "rolling" effect or an "ironing" effect to appose the material against the wall of the body lumen (from one side towards the other) or to smooth out the irregularities.

The directional balloon, in its inflated position, could provide and maintain an occlusive seal with at least a portion of the directional balloon. The occlusive seal is preferably placed distal to a region that needs medical intervention and therewith prevents unwanted materials from flowing distally. Examples of "unwanted materials" include clot, debris, plaque, endogenous or exogenous materials, or other material that may embolize or somehow cause partial or full obstruction of a body lumen. "Materials" that could be apposed are for instance, but not limited to, stents, coatings, surfaces, treatment-containing bodies, drug-coated materials, resorbable materials, delivery systems (for cells, genes or drugs), diagnostic or therapeutic materials, or the like. Furthermore, the balloon is connected to an inflating/deflating means (FIG. 38), which is common in the art of balloon catheters. Due to its directional inflation, the directional balloon provides a milking effect. A control means could be connected to the balloon and placed external to the patient to establish additional control over the milking action. The physician could for instance control the inflation/deflation action, the speed of inflation/deflation and/or the timing/intervals of inflation/deflation of the milking action. The physician could operate the milking action through a hand-free foot pedal, a touchscreen that is programmed to control a variety of milking parameters, or by voice recognition whereby the voice commands are associated with the milking parameters (See FIG. 38). In one aspect, the control of the milking action could be based on automation such that distinct points in the intervention (sensed by other tools being used or activated by a human operator) would automatically lead to adjustments in e.g. milking speed, timing or direction.

The balloon could be a single inflatable component that achieves the above features by having non-uniform, graded (continuous or stepwise) elasticity. The graded elasticity may also be achieved by situating a uniformly elastic balloon physically within the components (partial or full) of another uniformly elastic balloon (See FIG. 3), thus reducing elasticity at the doubled-over end by forcing inflation to work against a doubly thick expansive material. The graded elasticity may also be achieved by using a single material with non-uniform elasticity. The above features of the balloon could also be achieved by having a balloon with variable elasticity along its linear axis (See FIG. 3), by having different shapes, by having at least one non-uniform material, by having different layers potentially also with different elasticity, by having different diameters along its linear axis, or by having differently sized chambers potentially also with different elasticity.

The dimensions of the balloon are dependent on the type of application. For example, a suitable balloon for coronary interventions may require the diameter to be 1-4 mm, for carotid interventions the diameter to be 2-10 mm, for renal interventions the diameter to be 2-10 mm, for peripheral interventions the diameter to be 1-15 mm, or for neurovascular interventions the diameter to be smaller than 4 mm. The art of catheter balloons as well as the art of balloons in general teaches a variety of materials which could potentially be used to develop the balloon of the present invention. The type of material that could be used to manufacture the balloon should at least be flexible and biocompatible so that it can be used in a body lumen. However, the material of the balloon should be strong enough to provide an occlusive seal of at least the distal portion of the balloon with a body lumen when the balloon is either partially or fully inflated. The flexibility of the balloon is desired for providing the milking action of the balloon, which is aimed at liberating and milking away unwanted materials. Also, in a preferred embodiment, the balloon of the present invention should be able to accommodate a guidewire and is common in the art of balloon catheters, to advance, position and retract the balloon in a body lumen.

In another aspect of the invention, a suction catheter device is provided that includes a reversible suction trap system in which blood can be suctioned and partially or completely cleared. Removing unwanted materials or any substance could be based on size, charge, chemical consistency, filterability or removability. The main idea of the suction catheter of the present invention is to provide intermittent suction, which means that suction is applied during periods of a medical intervention in which there is a risk for embolization. When suction is discontinued, forward flow through the vessel may continue as normal. When suction is stopped or reversed in between periods of high embolic risk, a debris-containing filter may lapse off-line so that a continuous stream of filtered blood can re-enter the manipulated circulation.

In one aspect, the suction catheter may also include a reversibly expandable tip that allows approximation of the outer diameter of the catheter with the internal lumen of the vessel when suction is turned on (FIG. 40). In another aspect any type of biocompatible balloon could be used to partially or completely occlude the suction catheter with the body lumen aimed at providing optimal suction and removal of unwanted materials. In a preferred embodiment the suction catheter would be capable of removing particulates down to 15-40 µm in size, which are known to have destructive embolic potential. Orlandi et al. (in a paper entitled "*Characteristics of cerebral microembolism during carotid stenting and angioplasty alone*" and published in *Archives of Neurology*, Vol. 58(9), September 2001, 1410-1413) supports that there are short high-risk periods during carotid stenting and suggests that protection targeted at these times would be an optimal way of balancing prevention of embolic events with assurance of adequate distal blood flow.

The suction catheter preferably includes a control means (FIG. 39) to allow a user to control suction parameters. Examples of suction parameters are, for instance, but not limited to, suction on or off, the direction of suction (suction catheter static vs. suction actually reversed), the degree of suctioning (such as suction pressure, suction flow rate, etc.). The control of the suction catheter could be accomplished by means of a hand-free foot pedal, by means of a touchscreen that is programmed to control a variety of suction parameters of the suction catheter, or by voice recognition whereby the voice commands are associated with the suction parameters. In another aspect, the control of the suction catheter could be based on automation such that distinct points in the intervention (sensed by other tools being used or activated by the operator) would automatically lead to adjustments in e.g. suction intensity or direction. For example, advancement or extraction of a guidewire, directional balloon or instrument could be sensed and trigger the an action of the control unit of the suction catheter. In its preferred application, the suction catheter would be applied to interventions for the purpose of providing distal embolic protection. It would be applied intermittently during periods of high embolic risk, enabling forward (normal) blood flow to occur at all other (non-high-risk) times.

The suction catheter could have a tubular body, which could house a movable in-line filtration mechanism (FIG. 41). A filter could be used to separate unwanted materials from suctioned blood when it is flowing along it in one direction, but upon reversal of suctioning, the filter and its contents are repositioned off-line, such that suctioned blood (with or without filtered blood) are returned. In one aspect, one filter could be used. In another aspect more than one filter could be used to remove unwanted materials. The filter(s) could be positioned at the distal-most end to provide optimal filtration of the column of blood contained within the suction catheter. These filter(s) may also be arranged longitudinally along the length of the suction catheter. The filter(s) may also be attached or suspended within the suction catheter in such a manner as to necessitate filtration of blood passing through the catheter when it passes in one direction, but not the other direction.

These filter(s) may further be attached or suspended to the internal lumen of the suction catheter such that they are hinged at a point, allowing flow-directed engagement of the filter. These filter(s) could also be cleaned of particulate debris in between engagements or could be replaced (exchanged by fresh filter(s)) or renewed (cleaned of particulate debris) in between engagements, so as to provide optimal filtration with the start of each suctioning.

In case multiple filters are used they could be of equal, increasing, or decreasing pore-size. It would also be possible to have multiple filters, whereby only one filter is engaged during any given suctioning event. For example, during a procedure, a first filter is engaged during the first suctioning. When this suctioning is discontinued, the first filter (and its debris contents) is permanently disengaged. When suction is later resumed, a second (new) filter (which may be located distally or proximally along the longitudinal axis of the suction catheter) is engaged. After the second suctioning event is discontinued, the second filter (and all of its contents) is permanently disengaged, and so on.

Filters of sequential pore-size could also be used such that any one filter has a reduced chance of clogging with debris and occluding. In one aspect, a filter would have the largest pore size at the distal-most end of the catheter, and filters of progressively smaller pore sizes at the proximal end of the catheter. These filter(s) may be arranged radially within the suction catheter.

Figure 4:
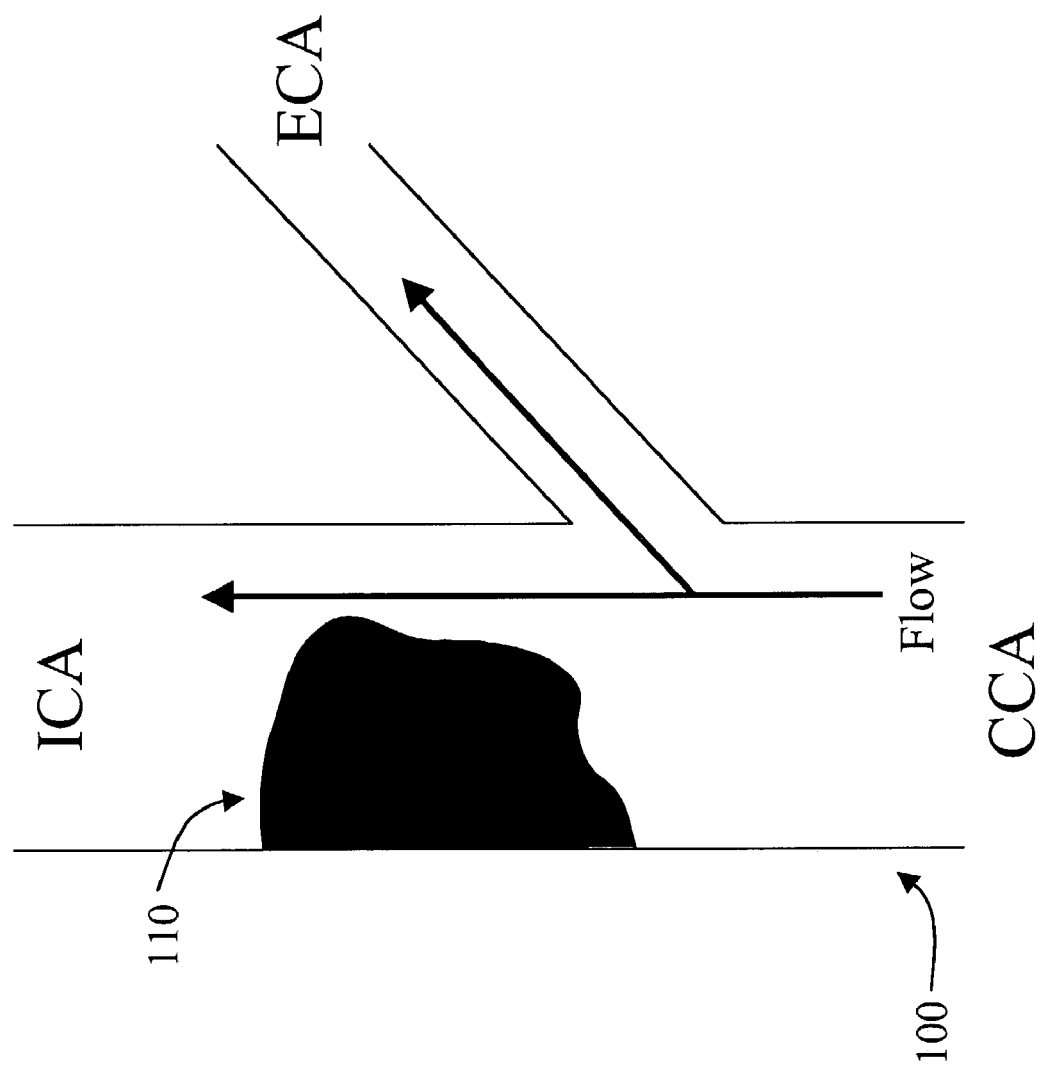
Figure 5:
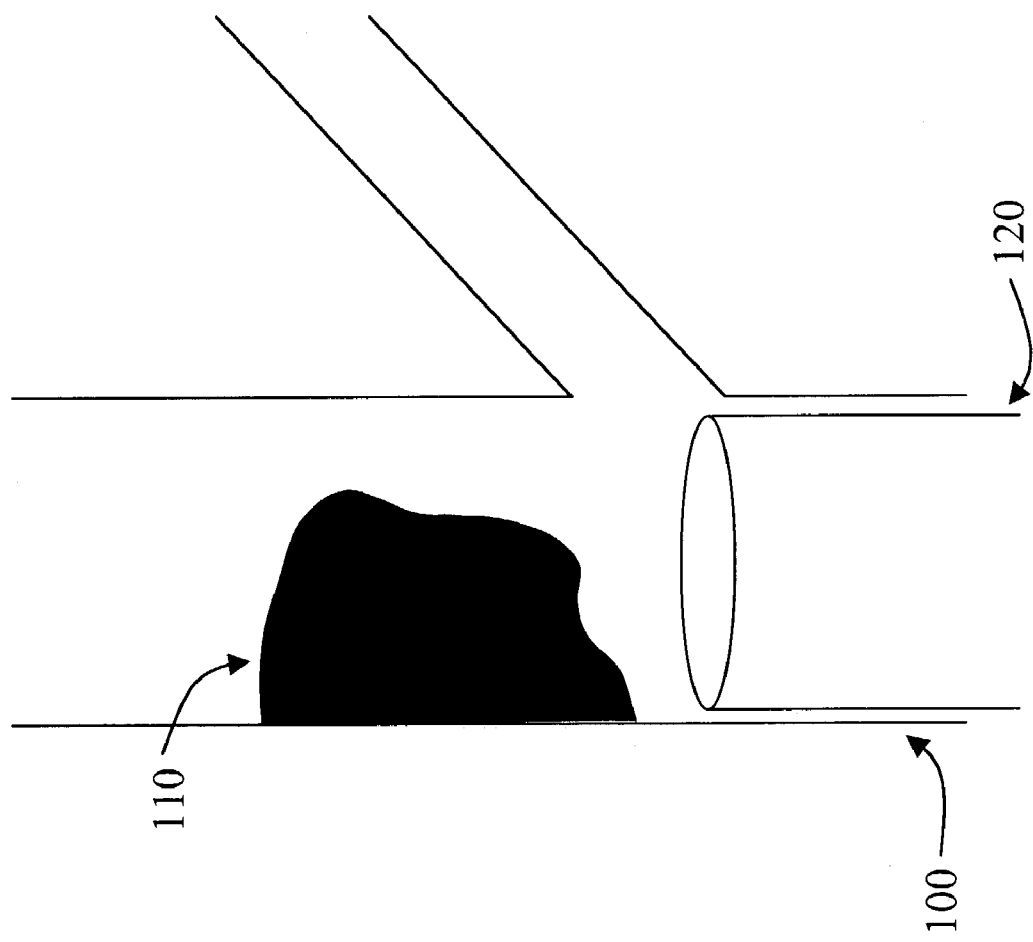
Figure 6:
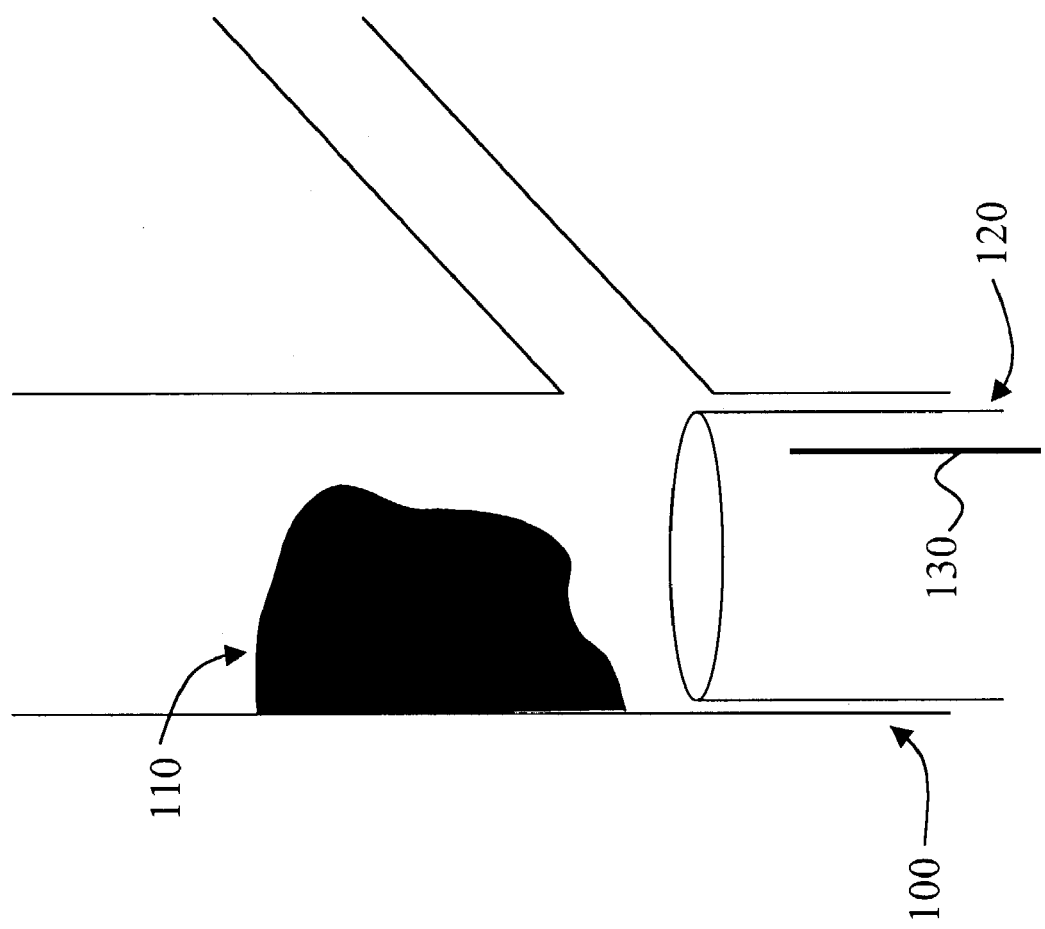
Figure 7:
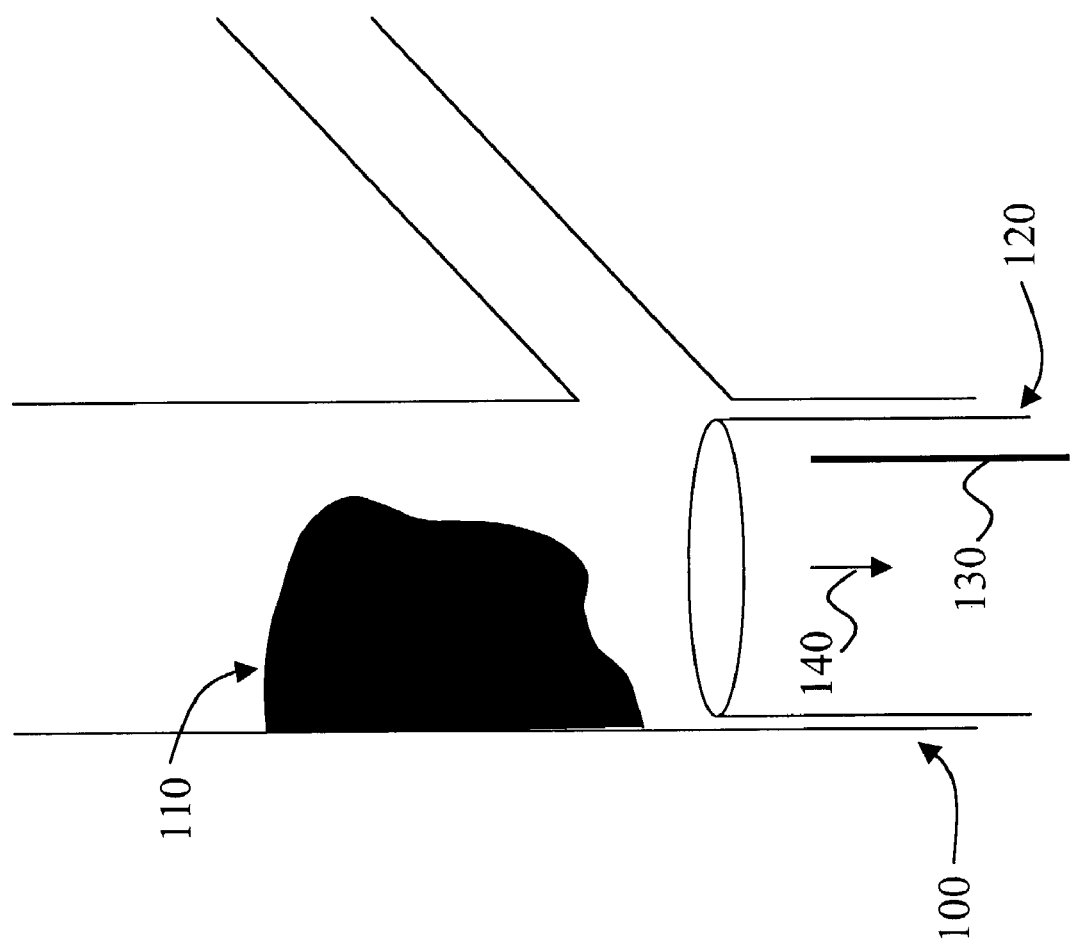
Figure 8:
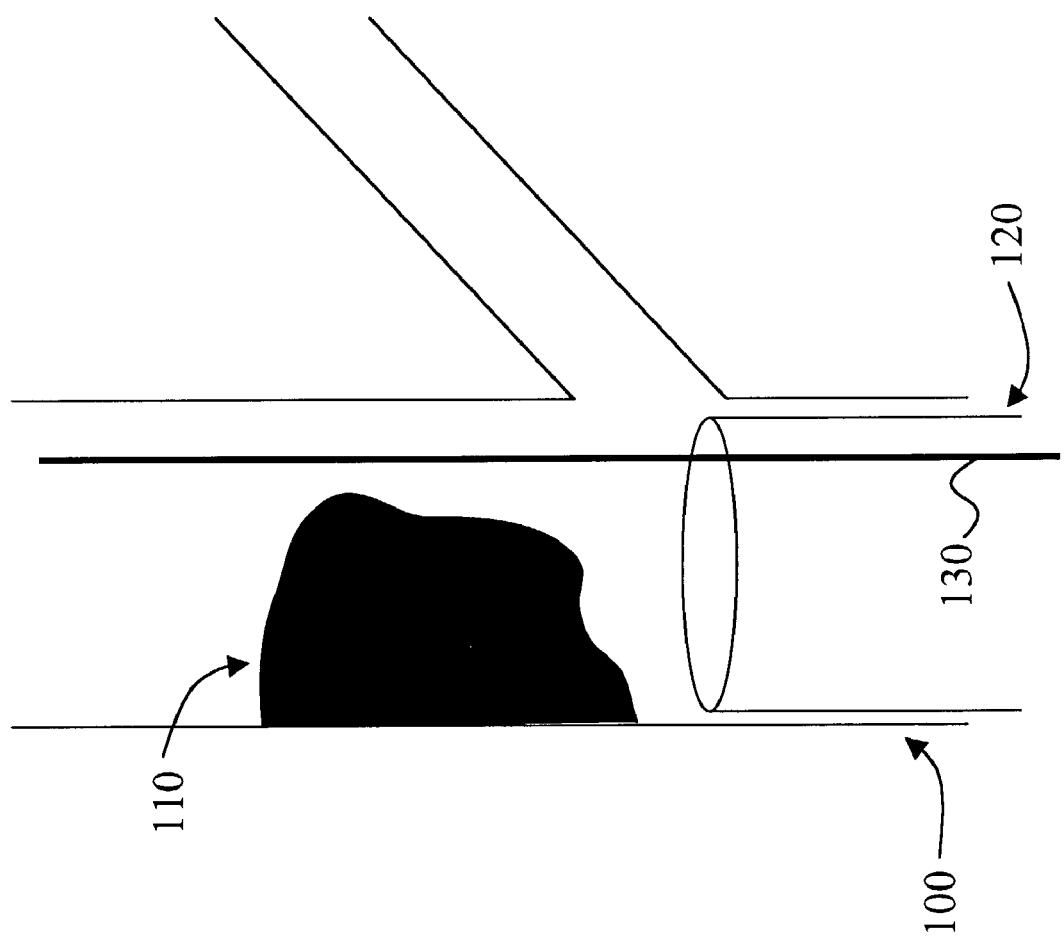
Figure 9:
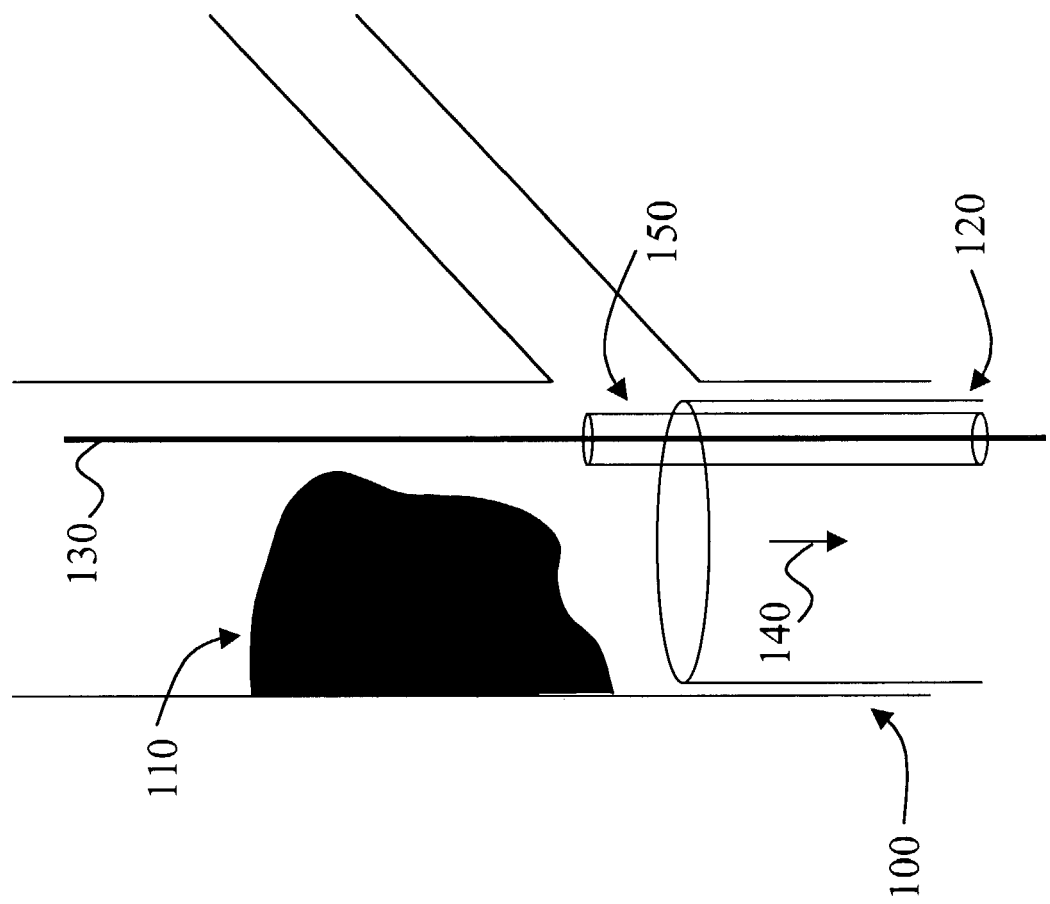
Figure 10:
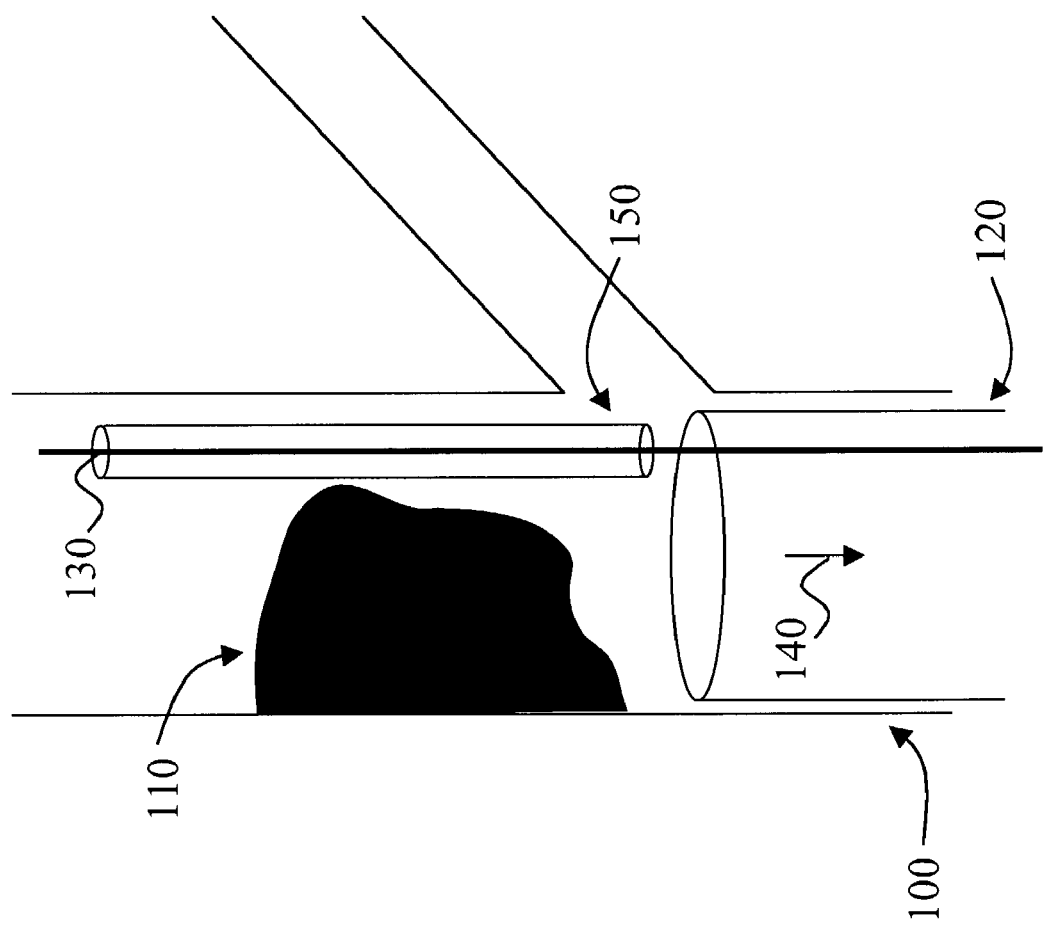
Figure 11:
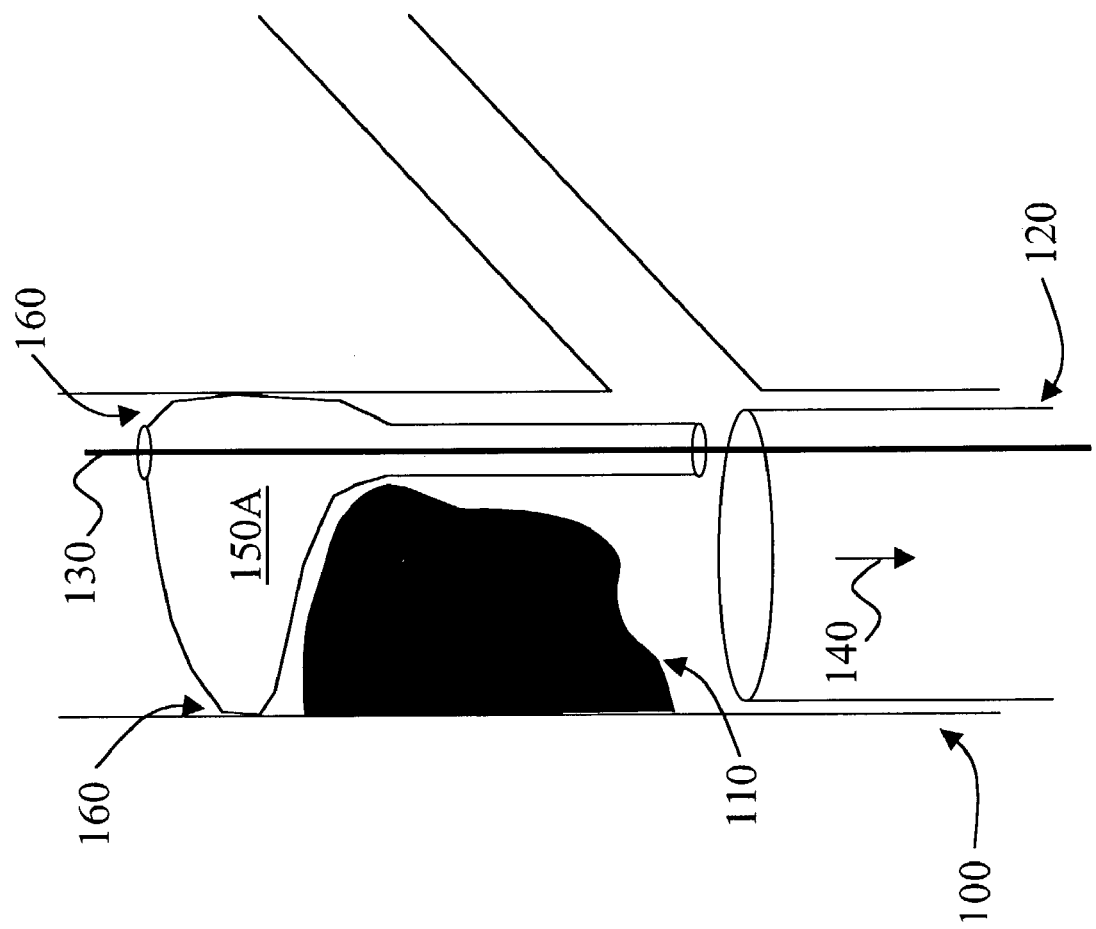
Figure 12:
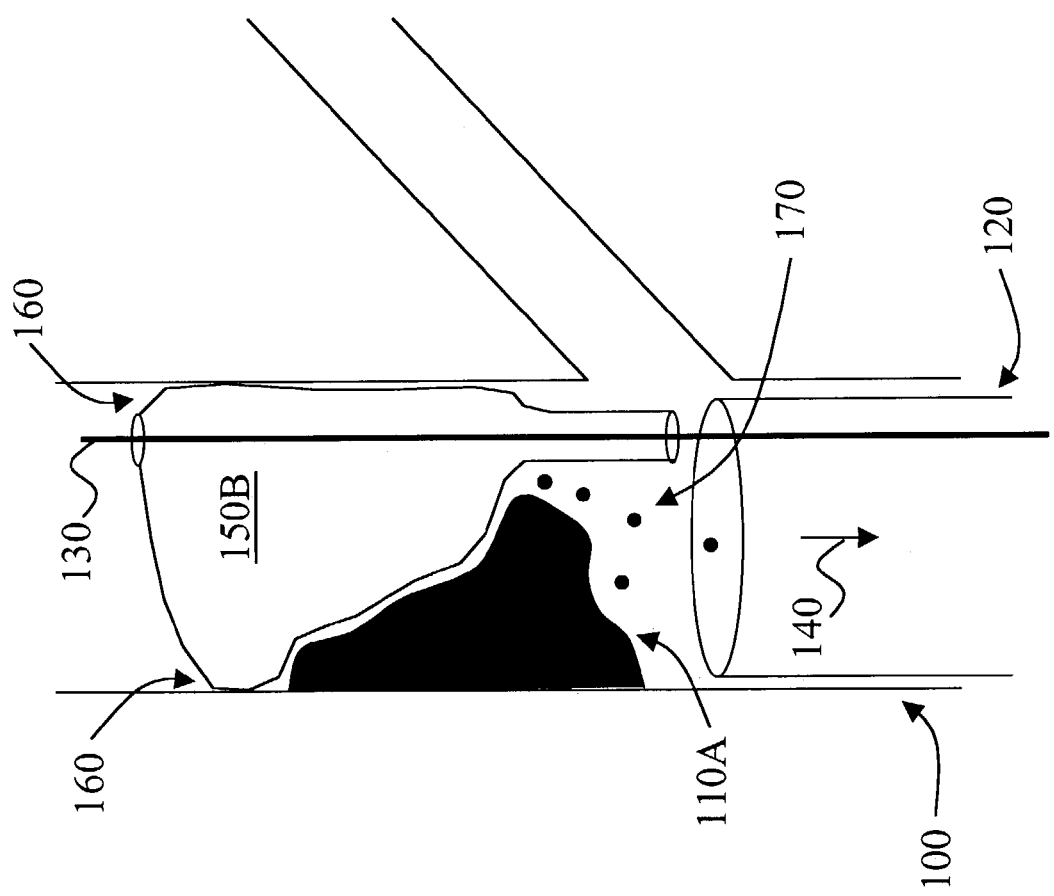
Figure 13:
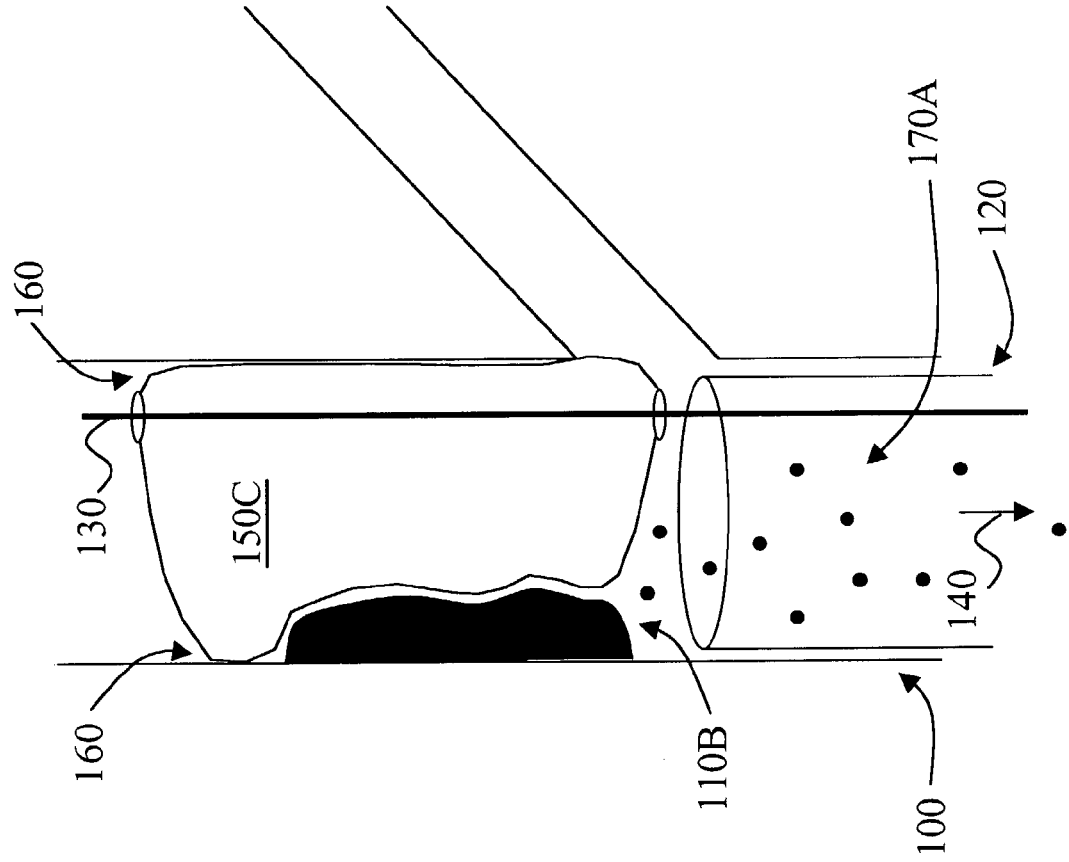
Figure 14:
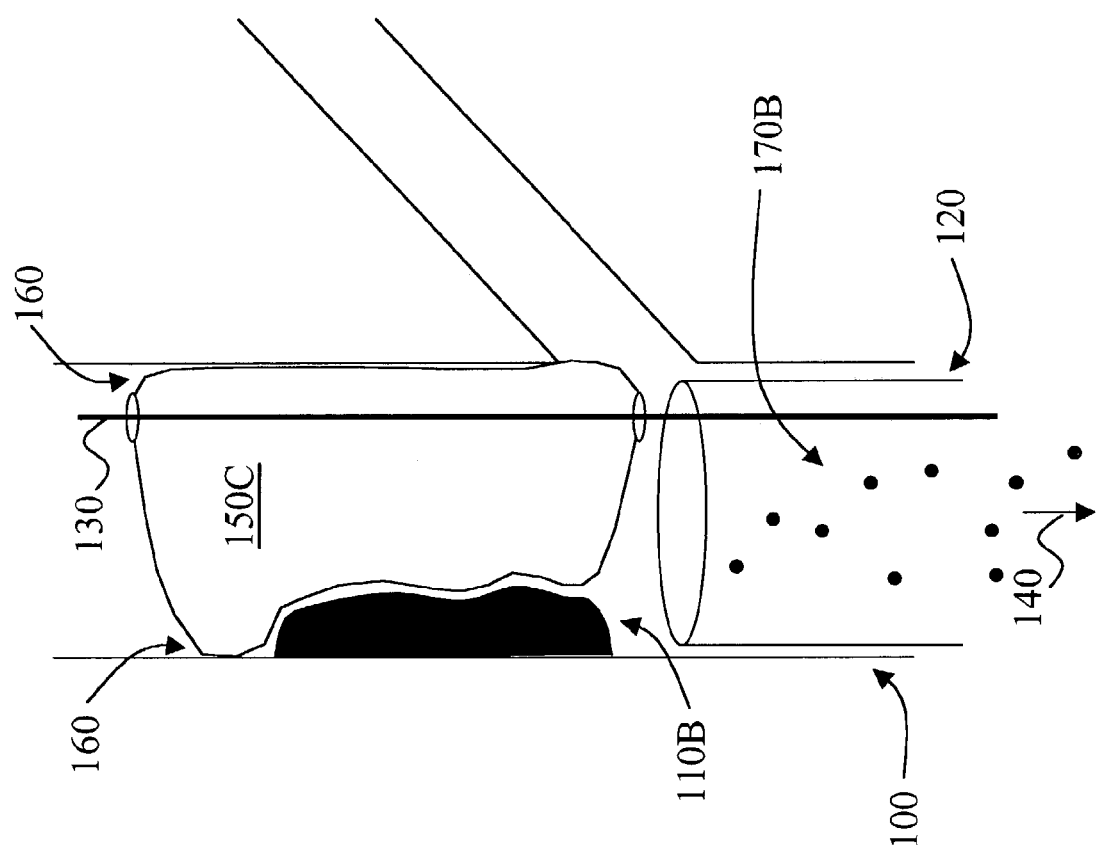
Figure 15:
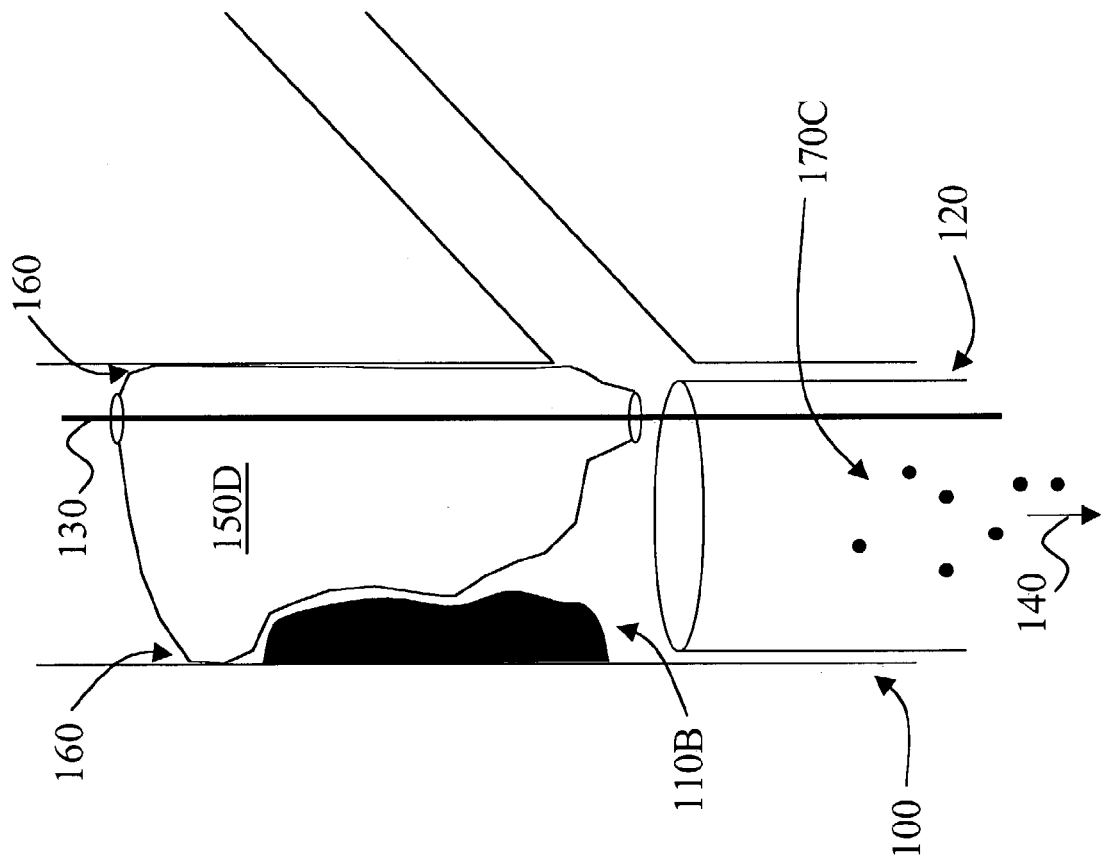
Figure 16:
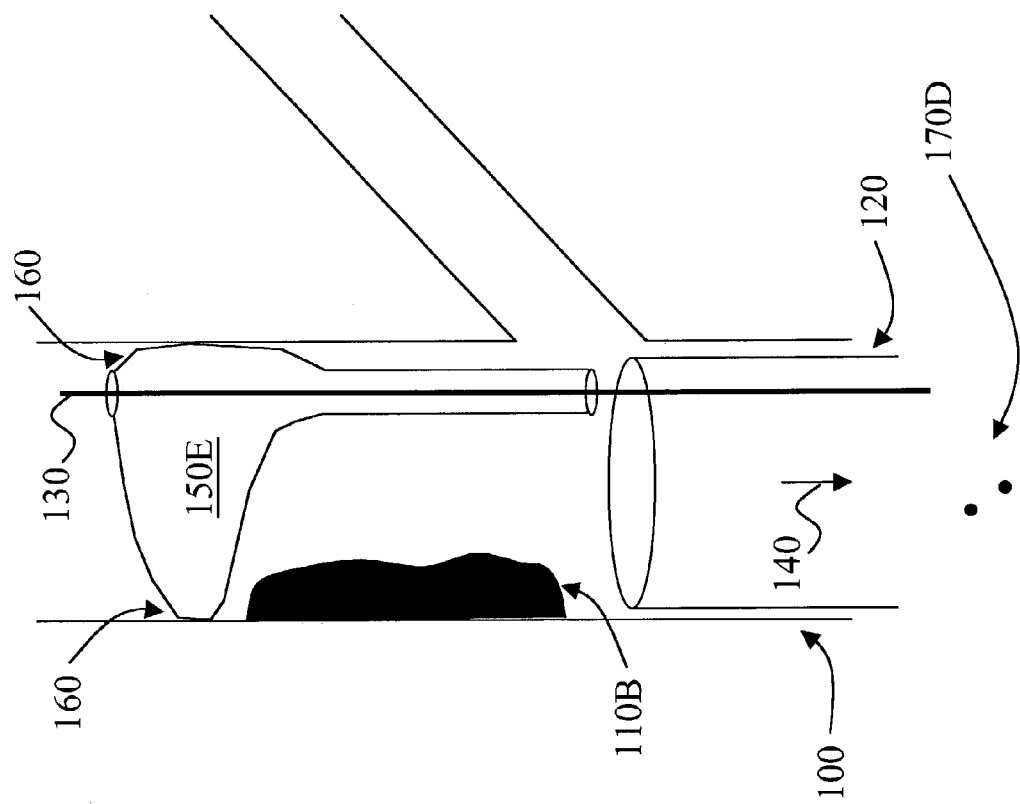
Figure 17:
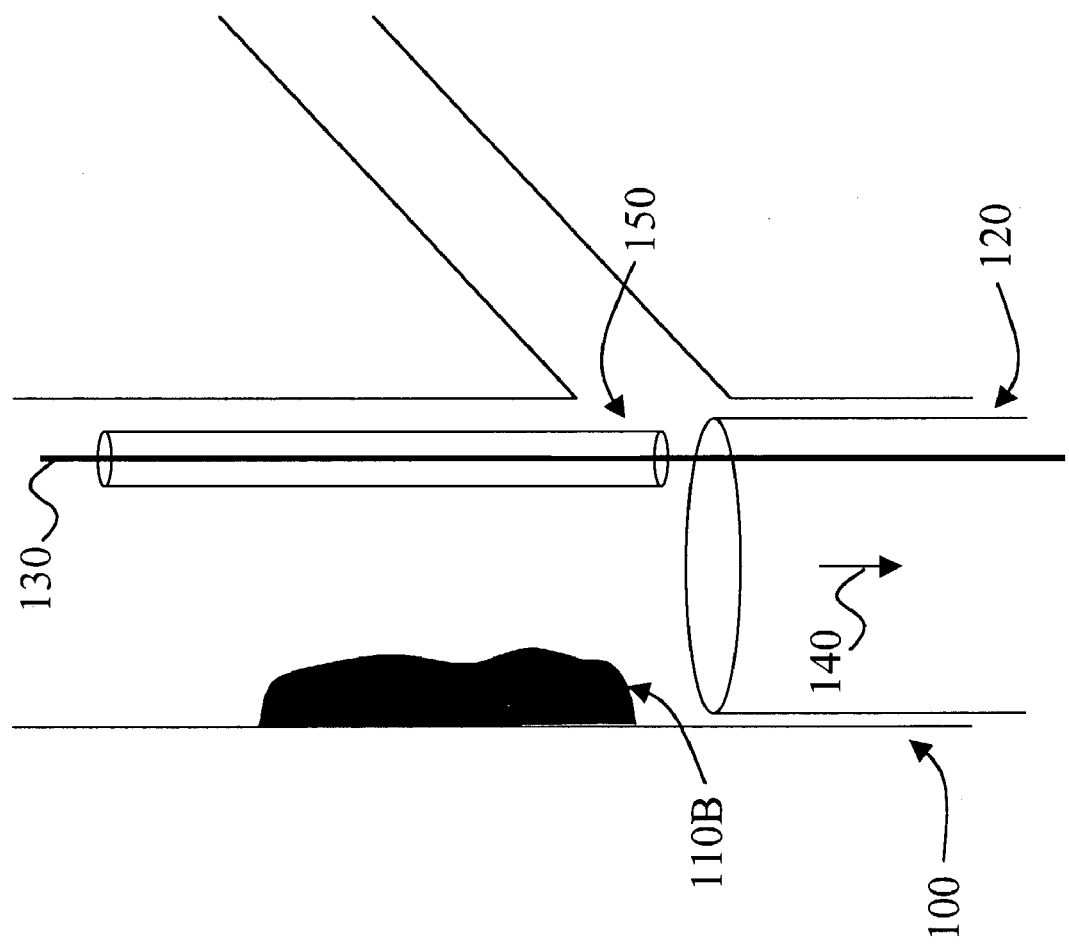
Figure 18:
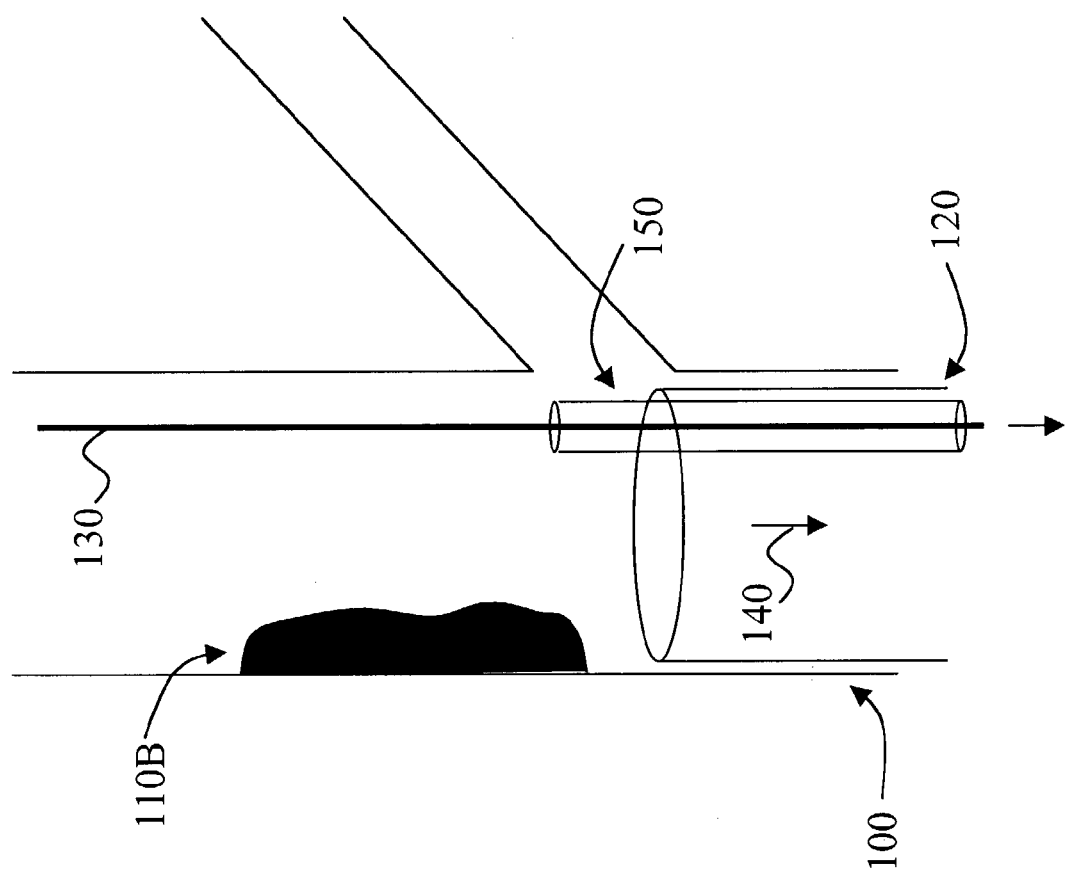
Figure 19:
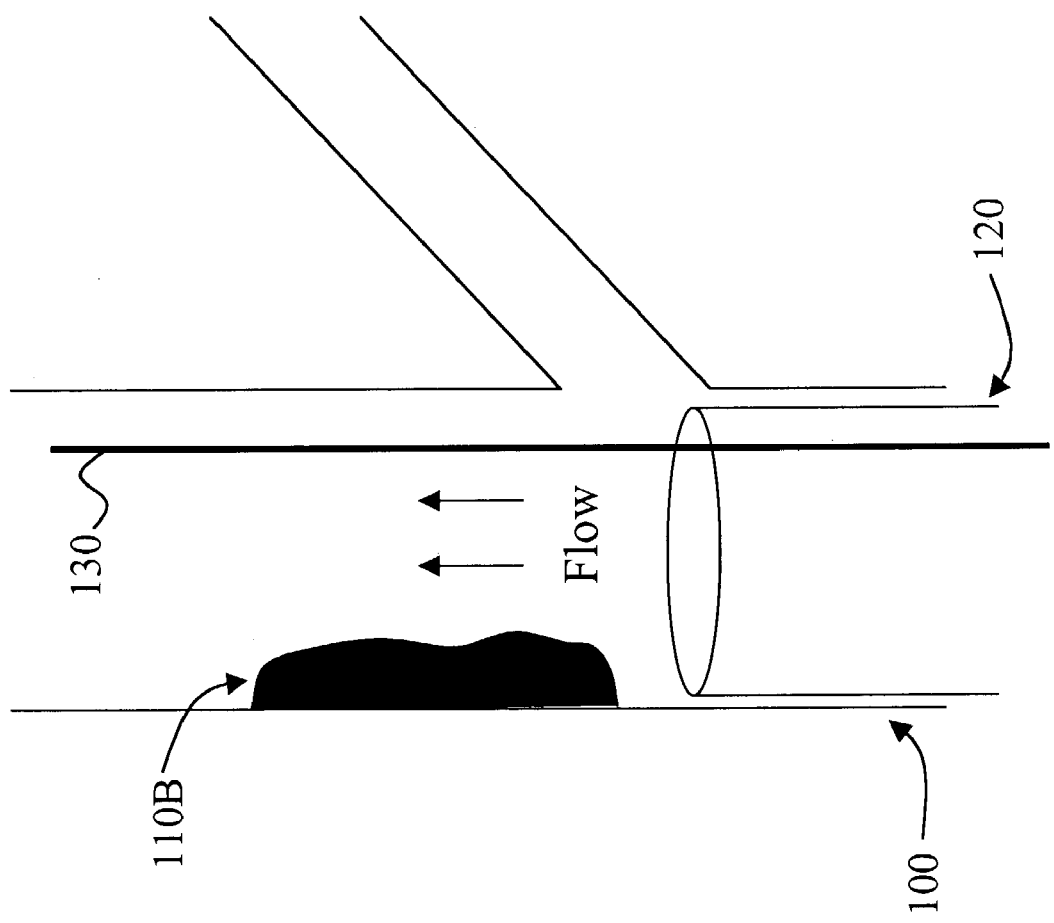

FIGS. 4-19 show an exemplary step-by-step scenario of an application of the directional balloon in a medical intervention that involves a carotid artery. As shown in FIG. 4 the carotid artery includes the internal carotid artery (ICE), the external carotid artery (ECA) and the common carotid artery (CCA). The carotid artery further shows a region that requires medical intervention. An example of such a region is for example an obstructive lesion. The examples shown in FIGS. 4-19 relate to a situation where it is necessary to protect against distal embolization and therefore a directional balloon is used that inflates in the distal to proximal direction and deflates in the proximal to distal direction. FIG. 5 shows the insertion of a suction catheter proximal to the lesion. Once the suction catheter is inserted, a guidewire will be advanced to a point just proximal to the lesion as shown in FIG. 6. Once the guidewire starts to cross the lesion, then suction is turned on as shown in FIG. 7. The suction could be turned off once the guidewire is in place (See FIG. 8) while the directional balloon is loaded inside the body lumen. The suction is turned back on just before crossing the lesion with the directional balloon (See FIG. 9) and while the directional balloon is being placed across the lesion (See FIG. 10). Key to achieving distal protection, the distal end of the directional balloon s positioned just beyond and distal to the region undergoing intervention (See FIG. 10). FIG. 11 shows the start of inflating the directional balloon, whereby an occlusive seal could be established with the body lumen, distal to the intervention region. During inflation of the directional balloon the suction is on (See FIGS. 11-14). This is important since the inflation might cause breakdown of unwanted materials from the lesion that one would like to prevent from moving distally. The directional balloon's milking action will direct any liberated unwanted materials toward a suction catheter so that they can be removed. FIGS. 15-17 show the deflation of the directional balloon in the proximal to distal direction during which the suction is kept on. Once the directional balloon is fully deflated, then it can be cleared from the lesion region (See FIG. 18). Suction is kept on until the directional balloon is cleared from the lesion region (See FIG. 19) after which time suction can be discontinued and forward flow restored while the directional balloon is removed from the body.

Figure 20:
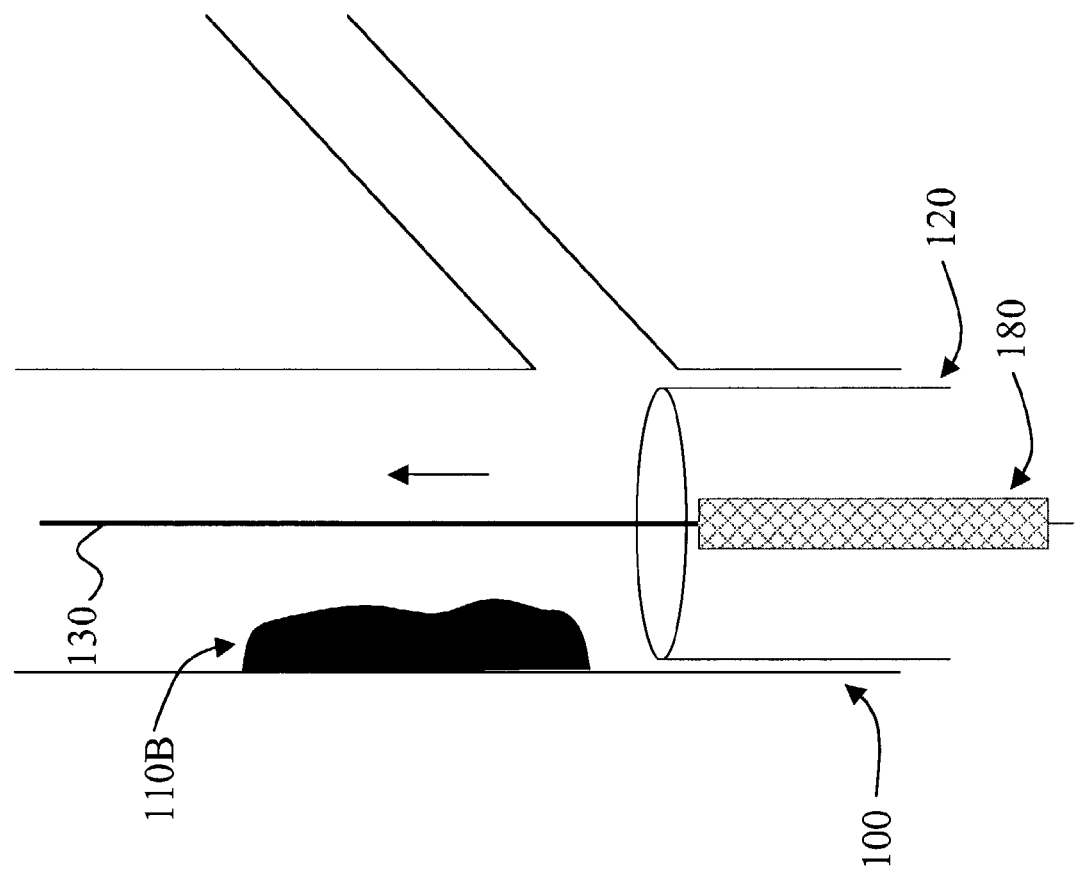
Figure 21:
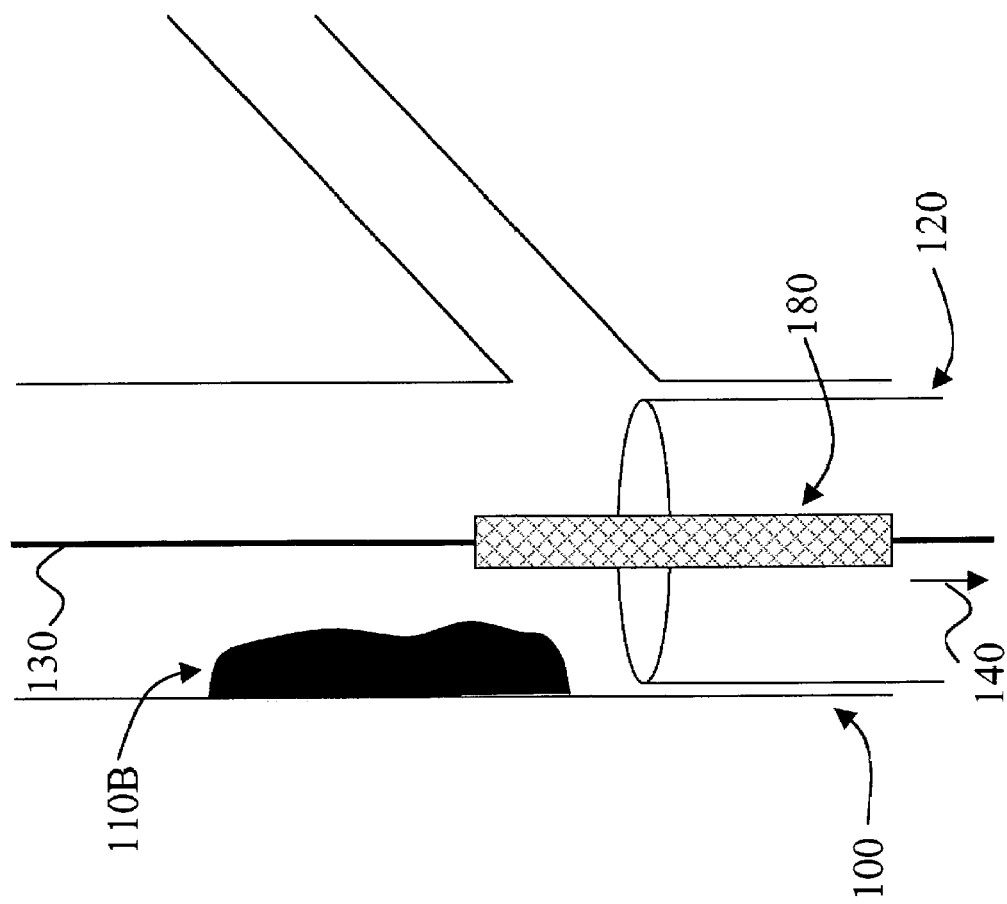
Figure 22:
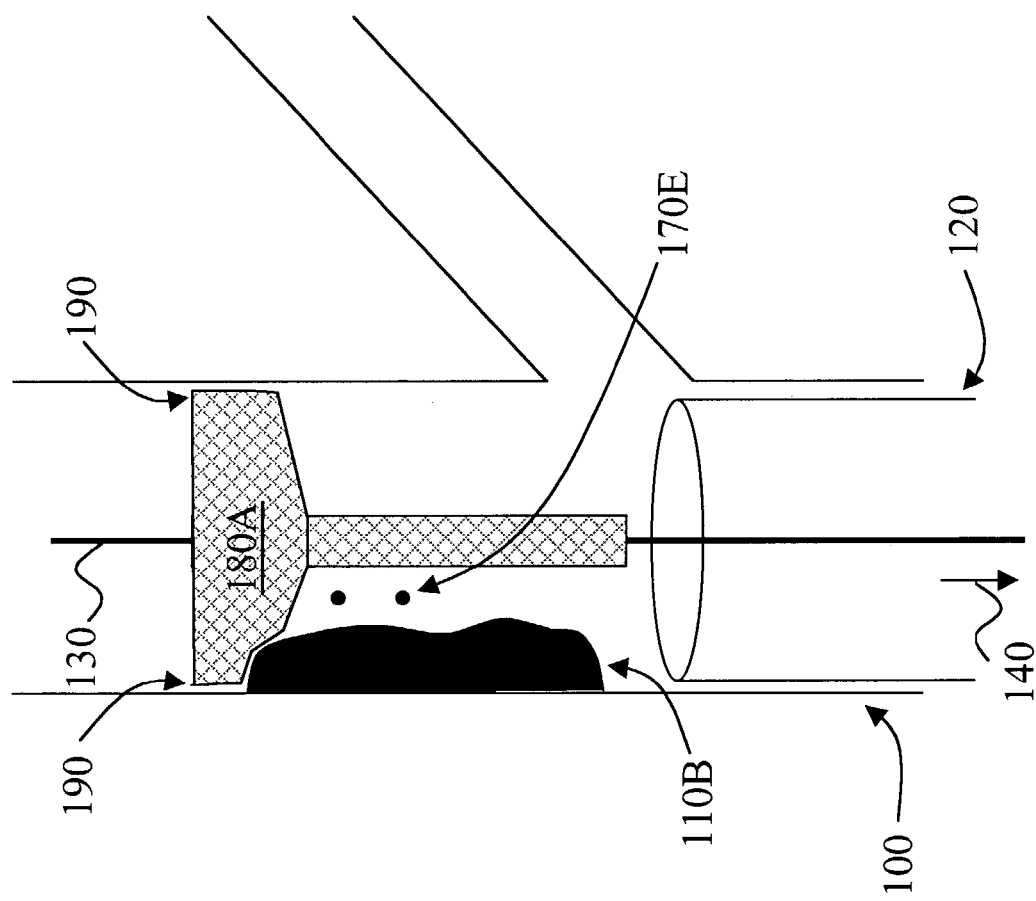
Figure 23:
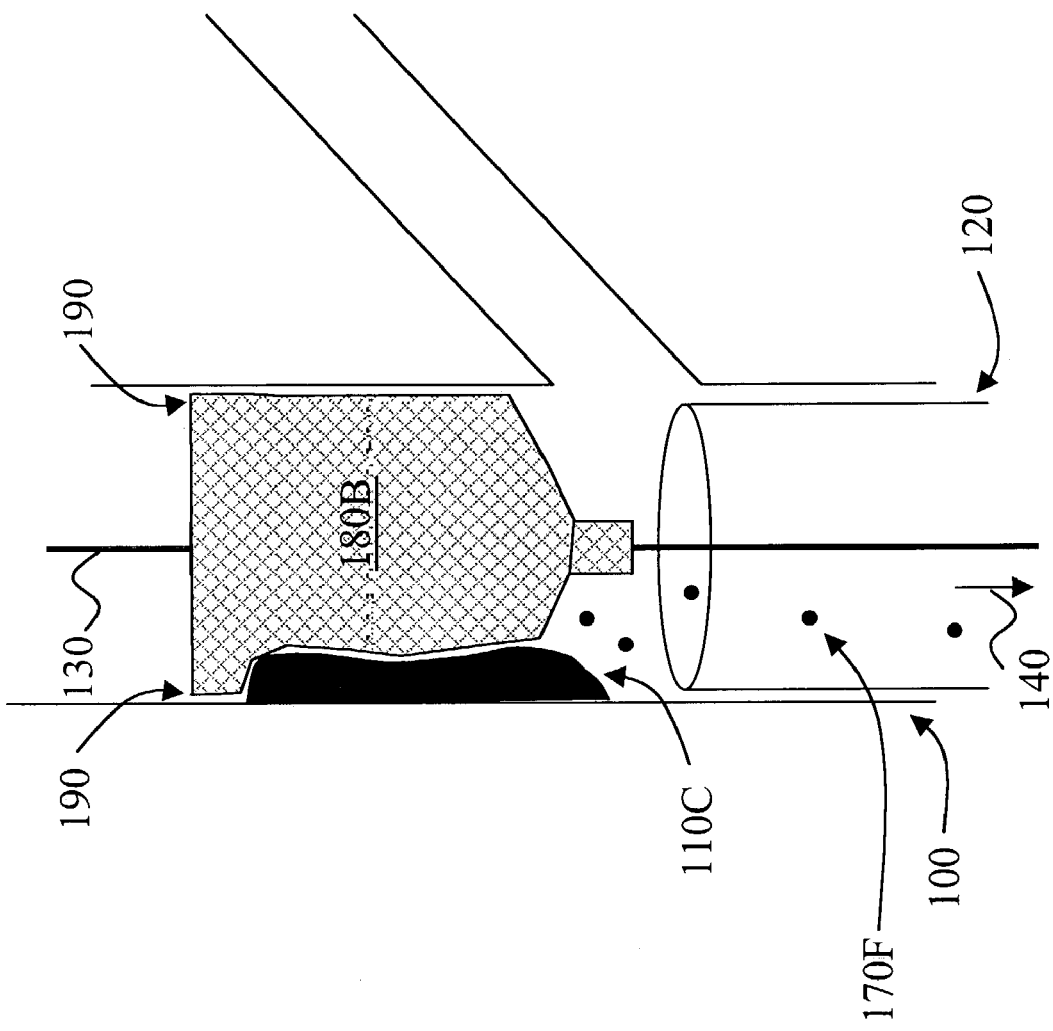
Figure 24:
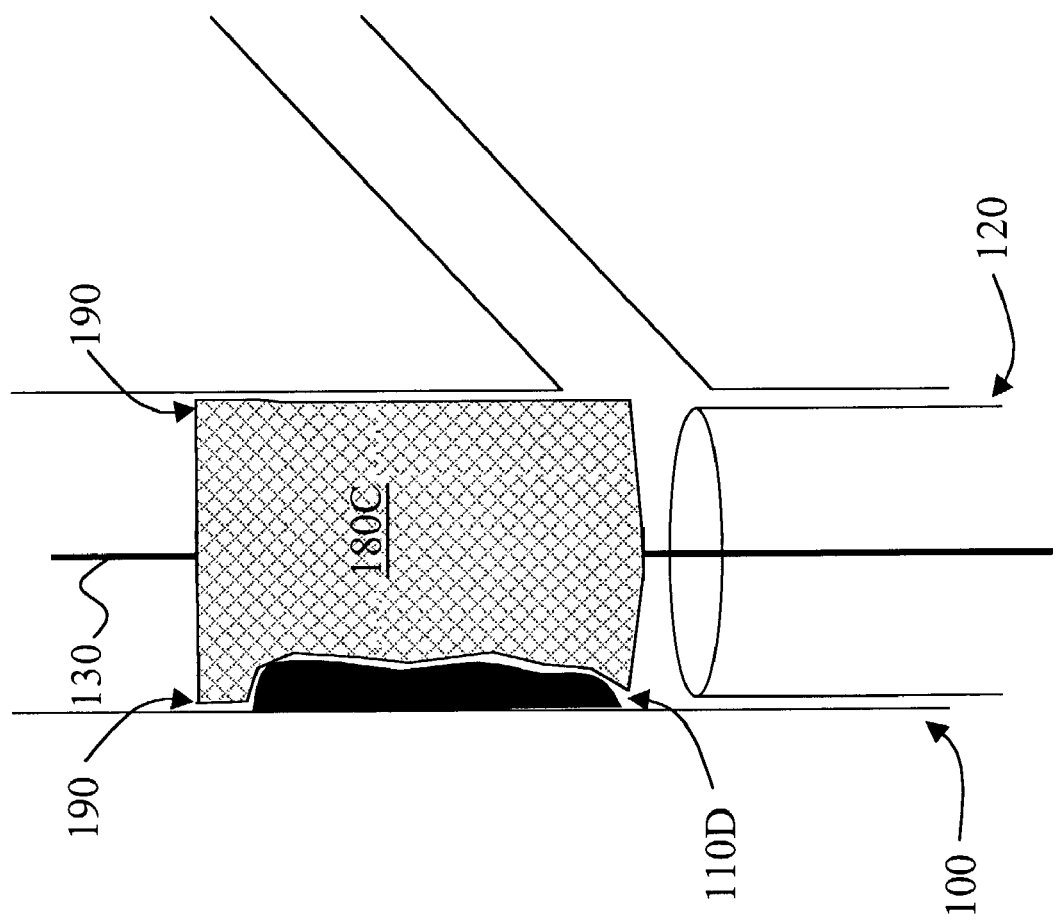
Figure 25:
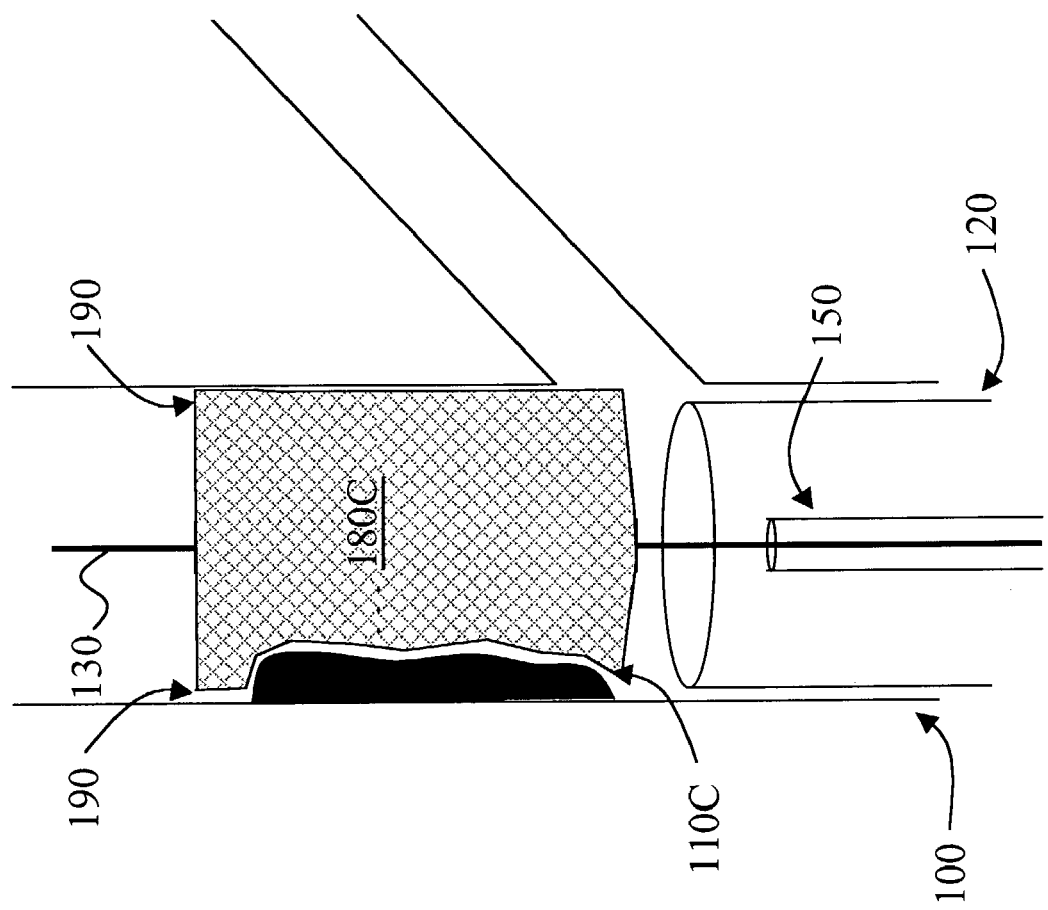
Figure 26:
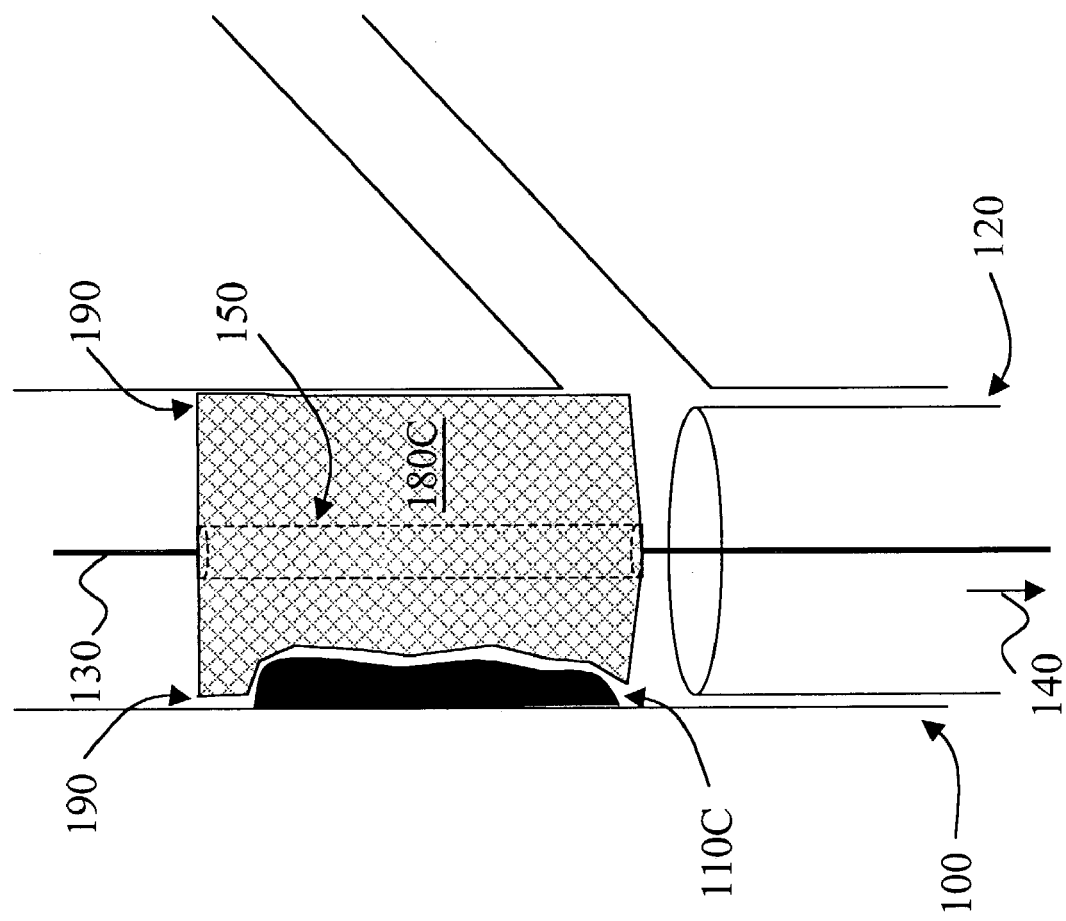
Figure 27:
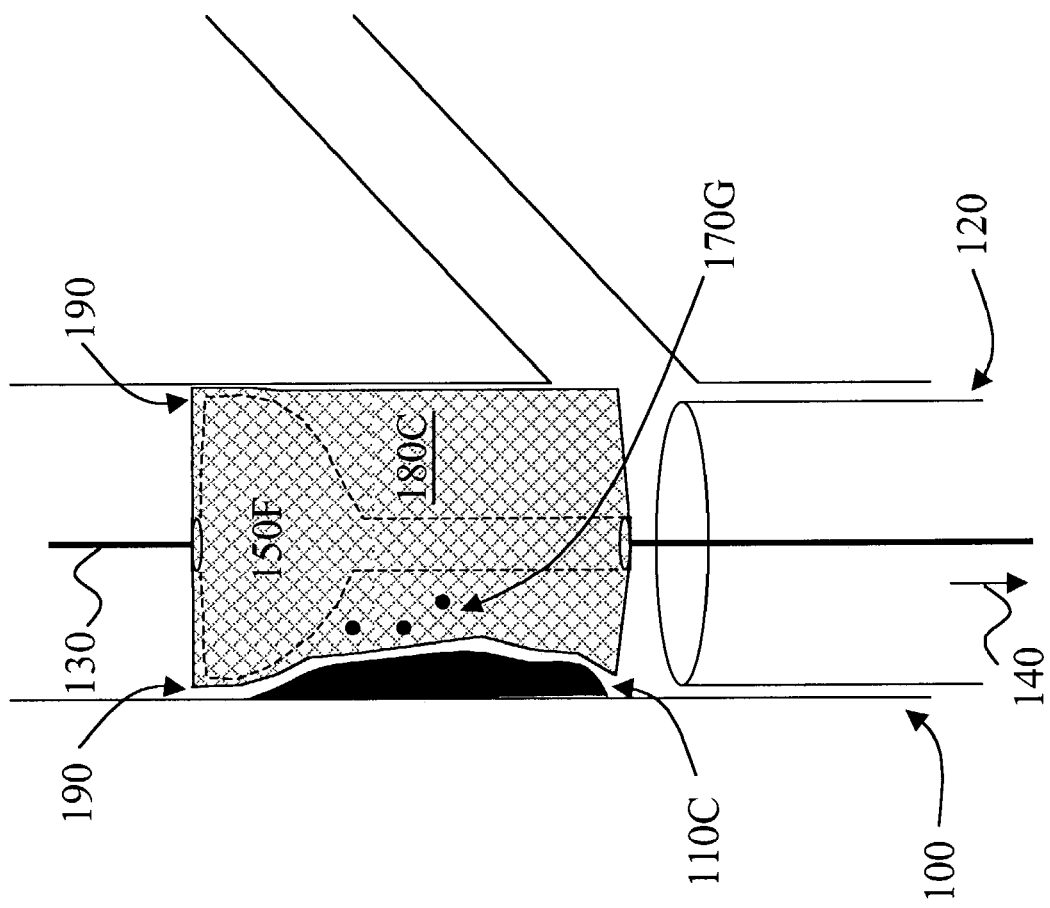
Figure 28:
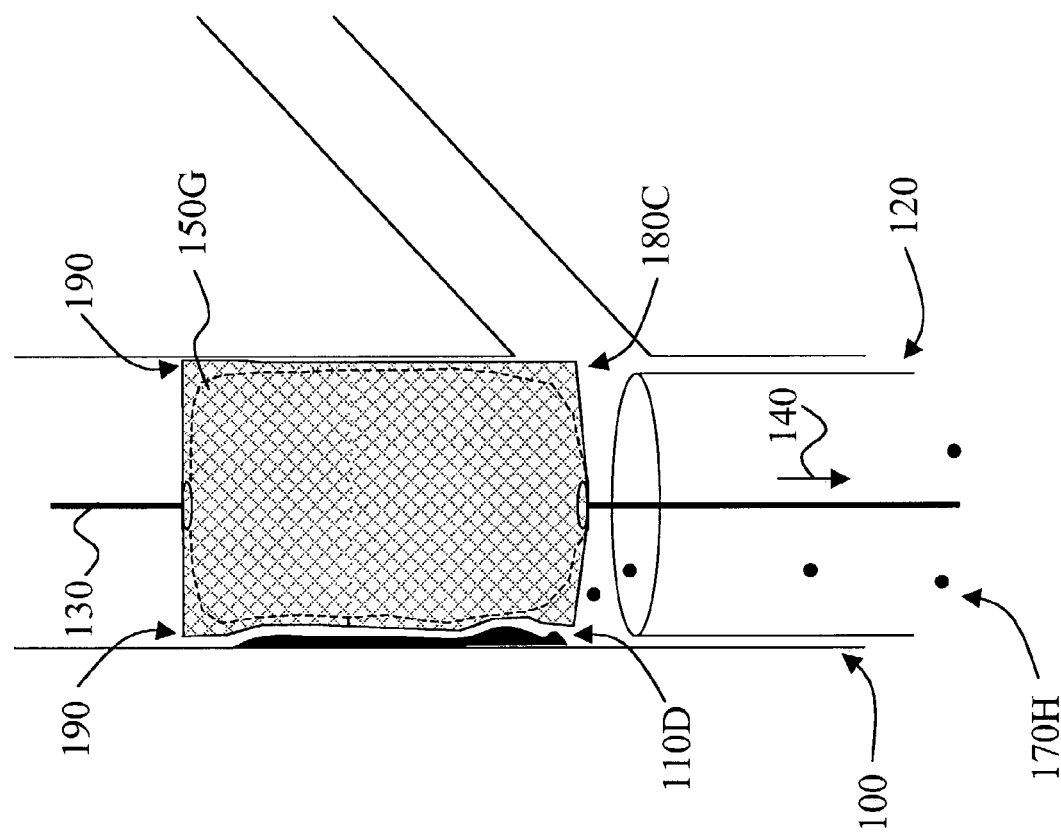
Figure 29:
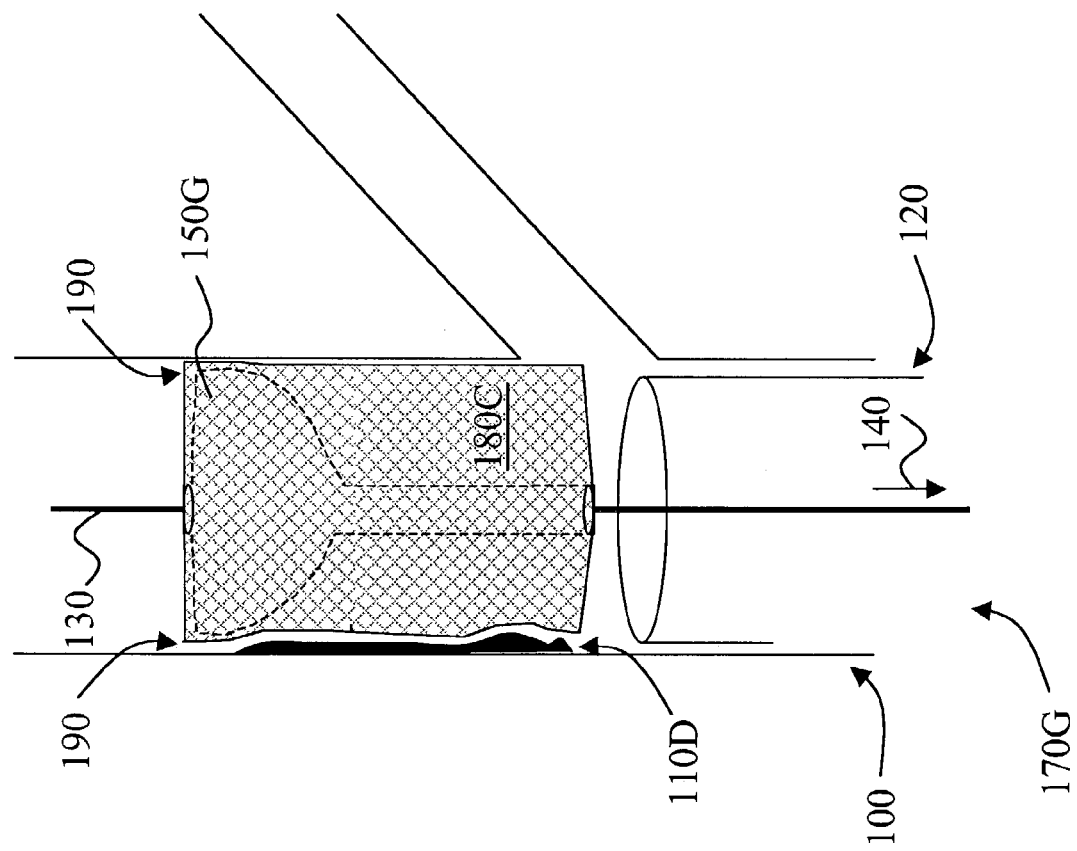
Figure 30:
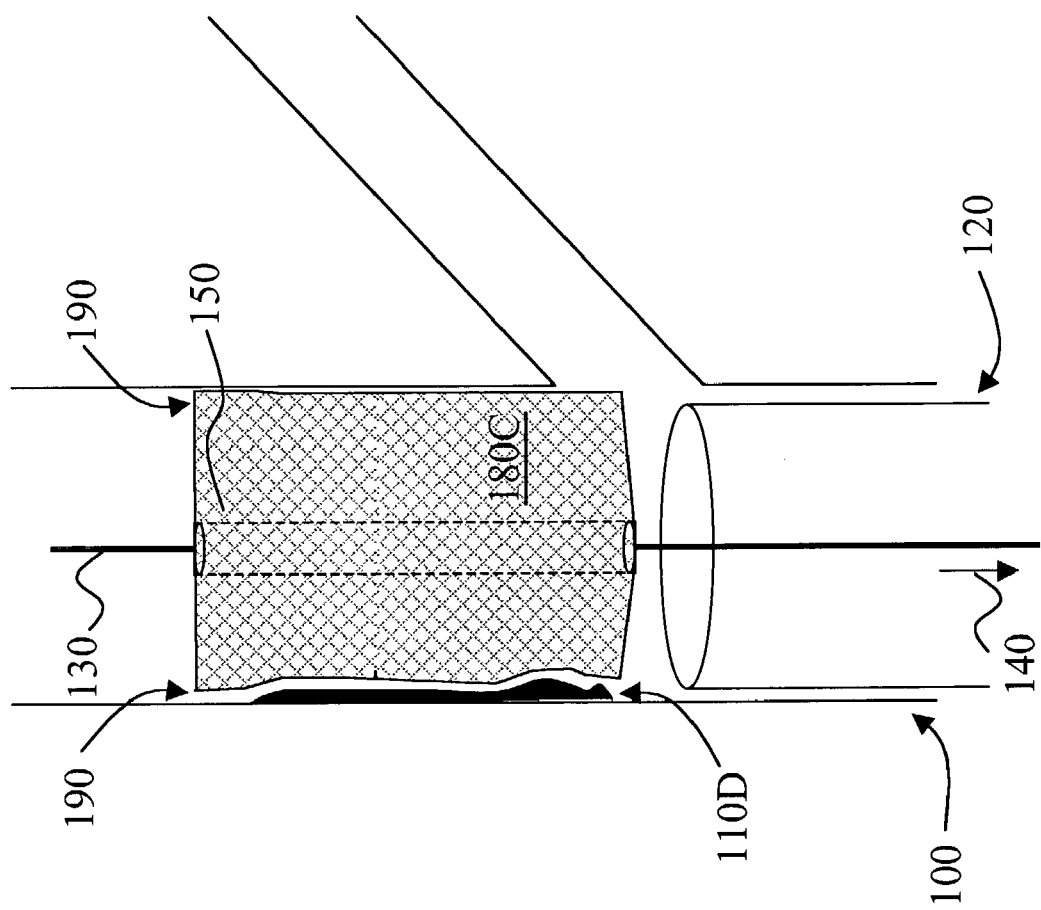
Figure 31:
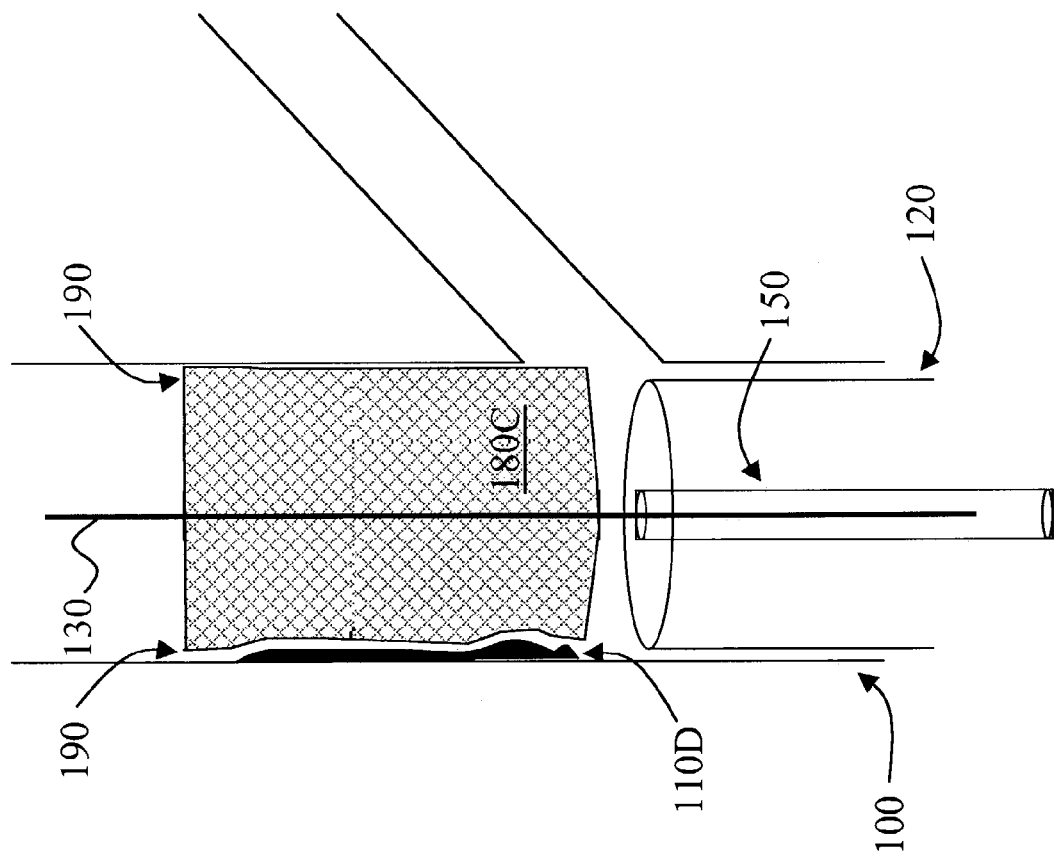

FIGS. 20-32 show an exemplary step-by-step scenario of an application of the directional balloon in a medical intervention that involves stenting a carotid artery. Under normal forward flow, a stent (e.g. a self-expandable stent) could be inserted to just proximal to the lesion as shown in FIG. 20. Suction is turned on during the advancement of the stent (See FIG. 21) and remains on until the full deployment of the stent across the lesion (See FIGS. 22-23) to remove unwanted materials. Once the stent is fully deployed across the lesion, the suction could be turned off (See FIG. 24). Normal flow could be restored while loading a directional postdilation balloon to just proximal to the lesion (See FIG. 25). Suction is turned back on while advancing and inflating the directional balloon (See FIG. 26). As shown in FIGS. 27-29, the inflation and/or deflation of the directional balloon could liberate unwanted materials. Suction is kept on to remove these unwanted materials. Still under suction, the directional balloon is then deflated (See FIG. 30), and then cleared from the lesion region. At this point, suction is turned off and forward flow restored in a similar fashion as described with respect to FIGS. 17-19. FIG. 31 shows suction is off while the directional balloon and guidewire and are being removed, restoring forward flow as shown in FIG. 32.

FIGS. 33-34 summarize the time course during which the suction catheter is controlled in terms of being on or off for each of the two exemplary step-by-step scenarios of applications of the directional balloon as described supra.

FIGS. 35-37 show an exemplary step-by-step scenario of an application of the directional balloon in a medical intervention that involves apposing a material to the wall of a body lumen. In one aspect, the material could be inserted inside the body lumen before the directional balloon. The material could be inserted using a guidewire, a deploying device or the like. In another aspect, the material could be removably attached to the outside of the directional balloon and inserted simultaneously. The present invention is not limited to any particular method of placing the material inside the body lumen. In one particular example, the material is a coating. The exemplary coating is in a poorly apposed state before it will be apposed by the directional balloon to the wall of the body lumen (See FIG. 35). FIGS. 36-37 show the inflation action of the directional balloon and the apposition of the coating to the wall of the body lumen. In this example, the direction of the inflation may not be important with respect to the body lumen, but could be in either direction (i.e. proximal to distal or distal to proximal). Again, the directional balloon provides a milking action to "roll" or "iron" the coating to the wall of the body lumen. It may be inflated and deflated once or repeatedly to achieve the desired effect.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, the suction catheter and directional balloon could be tailored to meet the unique dimensions and characteristics of other vascular and non-vascular applications. There are a number of different ways in which a directionally inflating balloon may be constructed and the present invention is not limited to the exemplary embodiments provided supra. The suction system may be configured for specific purposes with for instance an extracorporeal versus an intracorporeal blood reservoir.

The directional balloon may also be used for temporarily or permanently directing, manipulating, delivering, securing, extracting, or trapping something (e.g. unwanted materials, inserted devices, instruments, sensors, or the like) within a body lumen. The apposition could also be performed with two or more materials (one possibly being foreign to the body and one possibly being a body lumen) without air or fluid trapping. The directional balloon may also be used to obtain access to small, tortuous, difficult to access or cannulate lumens when access is obtained to one end of that body compartment.

All such variations are considered to be within the scope and spirit of the present invention as defined by the following claims and their legal equivalents.

What is claimed is:

1. A device for a medical intervention of a body lumen, comprising:

a directional balloon adapted to be positioned in said body lumen, wherein said directional balloon comprises only a single inflatable section between a proximal end and a distal end of said directional balloon and said directional balloon has varying elasticity between said proximal and distal ends, whereby the varying elasticity results in: (i) the radial inflation of said directional balloon being defined to radially inflate axially in a proximal to distal direction with respect to said directional balloon, and the radial deflation of said directional balloon being defined to radially deflate axially in a distal to proximal direction with respect to said directional balloon, or wherein (ii) the radial inflation of said directional balloon being defined to radially inflate axially in a distal to proximal direction with respect to said directional balloon, and the radial deflation of said directional balloon being defined to radially deflate axially in a proximal to distal direction with respect to said directional balloon.

2. The device as set forth in claim 1, further comprising a means to provide a milking action of said directional balloon.

3. The device as set forth in claim 1, wherein said directional balloon prevents distal embolization.

4. The device as set forth in claim 1, wherein said directional balloon is guided into said body lumen by means of a guidewire.

5. The device as set forth in claim 1, wherein said directional balloon comprises at least one non-uniform material.

6. The device as set forth in claim 1, wherein said directional balloon comprises different layers of materials.

7. The device as set forth in claim 1, wherein said directional balloon comprises different diameters along its linear axis.

8. The device as set forth in claim 1, wherein said directional balloon comprises a material that can be apposed to the wall of said body lumen.

9. A method for a medical intervention of a body lumen, comprising the step of:

providing a directional balloon having only a single inflatable section between a proximal end and a distal end of said directional balloon and said directional balloon having varying elasticity between said proximal and distal ends;

using said directional balloon in said body lumen; and inflating said directional balloon, whereby said inflation is defined to radially inflate said directional balloon axially in a proximal to distal direction with respect to said directional balloon, and the radial deflation of said directional balloon is defined to radially deflate axially in a distal to proximal direction with respect to said directional balloon, or wherein (ii) the radial inflation of said directional balloon is defined to radially inflate axially in a distal to proximal direction with respect to said directional balloon, and the radial deflation of said directional balloon is defined to radially deflate axially in a proximal to distal direction with respect to said directional balloon.

10. The method as set forth in claim 9, wherein said at least a portion of said directional balloon provides an occlusion seal with said body lumen.

11. The method as set forth in claim 10 wherein said occlusive seal is positioned distal to a region in said body lumen that requires said medical intervention.

12. The method as set forth in claim 9, further comprising the step of providing a milking action of said directional balloon.

13. The method as set forth in claim 9, wherein said directional balloon is placed across a region that requires said medical intervention.

14. The method as set forth in claim 9, further comprising the step of providing a suction means wherein said suction means is capable of providing a distal to a proximal suction to remove unwanted materials during periods of said medical intervention that risks distal embolization.

15. The method as set forth in claim 9, further comprising the step of providing a filter means to filter out unwanted materials from said body lumen.

16. The method as set forth in claim 9, wherein said directional balloon is used to appose a material to the wall of said body lumen.

17. The method as set forth in claim 9, wherein said directional balloon is used to manipulate unwanted materials within said body lumen.

18. The method as set forth in claim 9, wherein said directional balloon is used to manipulate an inserted device within said body lumen.

* * * * *